(12) United States Patent
Aplin et al.

(10) Patent No.: US 11,571,483 B2
(45) Date of Patent: Feb. 7, 2023

(54) E2F REPORTER MELANOMA CELLS

(71) Applicant: THOMAS JEFFERSON UNIVERSITY, Philadelphia, PA (US)

(72) Inventors: Andrew Aplin, Moorestown, NJ (US); Jessica Teh, Philadelphia, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 327 days.

(21) Appl. No.: 17/011,015

(22) Filed: Sep. 3, 2020

(65) Prior Publication Data

US 2021/0194941 A1 Jun. 24, 2021

Related U.S. Application Data

(60) Continuation of application No. 15/851,103, filed on Dec. 21, 2017, now Pat. No. 10,645,128, which is a division of application No. 15/009,464, filed on Jan. 28, 2016, now Pat. No. 9,880,150.

(60) Provisional application No. 62/108,886, filed on Jan. 28, 2015.

(51) Int. Cl.
*C12Q 1/68* (2018.01)
*A61K 49/00* (2006.01)
*G01N 33/50* (2006.01)

(52) U.S. Cl.
CPC ...... *A61K 49/0008* (2013.01); *G01N 33/5011* (2013.01); *G01N 33/5041* (2013.01)

(58) Field of Classification Search
CPC .......... A61K 49/0008; G01N 33/5011; G01N 33/5041

See application file for complete search history.

(56) References Cited

U.S. PATENT DOCUMENTS

| | | | |
|---|---|---|---|
| 8,202,886 | B2 | 6/2012 | Cress et al. |
| 8,822,421 | B2 | 9/2014 | Bertino et al. |
| 8,841,274 | B2 | 9/2014 | Lathangue |
| 8,877,445 | B2 | 11/2014 | Shackney |
| 9,880,150 | B2 | 1/2018 | Alpin et al. |
| 2003/0059794 | A1 | 3/2003 | Vogels et al. |
| 2005/0239095 | A1 | 10/2005 | Lu et al. |
| 2005/0245473 | A1 | 11/2005 | Saunders |
| 2009/0081645 | A1 | 3/2009 | Kotani et al. |
| 2010/0240126 | A1 | 9/2010 | Lin et al. |
| 2016/0000940 | A1 | 1/2016 | Moore et al. |
| 2018/0100204 | A1 | 4/2018 | O'Shea et al. |
| 2018/0180594 | A1 | 6/2018 | Alpin et al. |

FOREIGN PATENT DOCUMENTS

WO 2003051312 A2 6/2003

OTHER PUBLICATIONS

TdTomato—Our Brightest Red Fluorescent Protein, Clontech Laboratories, Inc., 2008.

*Primary Examiner* — Catherine S Hibbert
(74) *Attorney, Agent, or Firm* — Cozen O'Connor

(57) ABSTRACT

A modified melanoma cell line capable of quantification of the effects of MEK inhibitors and CDK4/6 inhibitors in a quantitative, temporal and non-invasive manner both in vitro and in vivo.

6 Claims, 29 Drawing Sheets

E2F REPORTER MELANOMA CELLS

CROSS REFERENCE TO RELATED APPLICATIONS

This application is a continuation of U.S. application Ser. No. 15/851,103, filed Dec. 21, 2017, which is a divisional of U.S. application Ser. No. 15/009,464, filed Jan. 28, 2016, which claims the benefit of U.S. Provisional Application Ser. No. 62/108,886, filed Jan. 28, 2015, which are hereby incorporated by reference in their entirety.

FIELD OF INVENTION

The present application is generally related to modified reporter cells and methods of testing and/or detection of inhibitory compounds for efficacy in inhibiting E2F-mediated activity. In particular, methods including an assay to assess the efficacy of a cyclin-dependent kinase (CDK) inhibitor to block E2F signaling that is non-invasive, and provides quantitative results in a non-bias manner, that is capable of monitoring activity across the whole of the tumor.

BACKGROUND OF THE INVENTION

Typically, aberrant cell cycle is a hallmark of cancer. A major challenge in oncology treatment is to identify compounds that target specific tumor types in order to minimize toxicity and to maximize efficacy to the targeted tumor.

In the oncology field, it is common to identify tumor types using microscopic histopathological appearance of fixed and stained tumor samples, and to use systems such as the tumor-node-metastasis system to determine the clinical spread of the tumor. This, and other systems, evaluate the size of the tumor, the presence or absence of the tumor in the lymph nodes, and the presence or absence of metastases to assign a stage to the tumor. The tumor type and the stage are then frequently utilized to select appropriate therapy and to determine prognosis for the patient.

E2F transcription factors control the expression of many genes and play a major role during the G1-S transition in the cell cycle. Several assays currently exist that allow for testing of E2F inhibition; however, these assays suffer from several problems.

For example, current assays are frequently invasive, in that they require significant sampling of a tumor tissue. Other assays are not quantitative, that is, they may report a yes or no answer, but are unable to appropriately quantify and measure, in a non-bias manner, the amount or percentage of block of E2F signaling. Furthermore, current assays require that the experiment is terminated at the time of sample retrieval and therefore cannot be utilized to test E2F activity in a temporal manner.

Accordingly, there is a need to identify new methods and materials that are suitable for determining the efficacy of an inhibitor to block E2F signaling in a non-invasive manner and which is quantitative in a non-bias manner so as to properly identify and quantify the amount of block on a particular inhibitor.

SUMMARY OF THE INVENTION

In accordance with these and other objects, a first embodiment of an invention disclosed herein is a transduced cancer cell comprising an EGFP-firefly luciferase fusion gene, under the control of E2F transcriptional response elements, wherein the cell is suitable for testing the ability of a compound to block E2F signaling and to quantify the level of block against a control.

An embodiment is directed to a method for determining the efficacy of a compound of interest to inhibit E2F activity comprising: applying a compound of interest to a modified cell, wherein said melanoma cells harboring either BRAF/NRAS mutations or neither mutations involving a modified E2F reporter system to monitor the efficacy of CDK4/6 inhibitor-based therapies, wherein tumor cells are transduced with tdTomato fluorescent protein and an EGFP-firefly luciferase fusion gene under the control of E2F transcriptional response elements; determining the amount of tdTomato activity and determining the amount of firefly luciferase activity in the modified cell, and comparing the amount of tdTomato to the amount of firefly luciferase expression, to quantitate E2F reporter activity to tumor size, wherein tdTomato measures tumor size and firefly luciferase measures pathway activity in the tumor.

A further embodiment is directed to a high-throughput in vitro screening method for determining inhibition of E2F comprising: loading reporter cells comprising an E2F response element-EGFP-firefly luciferase construct onto a screening plate, mixing at least one compound of interest in a test vehicle, administering to at least one cell on said screening plate the compound of interest, administering to at least a second cell, the test vehicle, incubating said cells for a predetermined amount of time, comparing the amount of firefly luciferase activity to the level of actin/tdTomato activity between the compound of interest and of the test vehicle in the incubated cells, and quantifying the level of block for the cells treated with the compound of interest, by normalizing firefly luciferase activity to tdTomato activity/actin levels.

A further embodiment is directed to a kit for testing and determining efficacy of a compound to inhibit E2F activity comprising: (1) E2F response elements-EGFP-Firefly luciferase plasmid/lentivirus, and (2) tdTomato fluorescent protein plasmid/lentivirus, wherein, the firefly luciferase and tdTomato fluorescent protein are transduced into a cancer cell to generate a reporter cell line of interest.

A further embodiment is directed to a kit for transducing a cancerous cell, comprising (1), E2F response elements-EGFP-firefly luciferase construct and (2), tdTomato fluorescent protein, wherein the E2F construct and tdTomato protein can be transduced into a cancer cell, wherein said cell can be suitably used in in vitro or in vivo screening to test a compound for its ability to inhibit the E2F pathway and to quantify the level of block of the same.

A further embodiment is directed to a method to monitor the efficacy of a compound on the E2F Pathway, including CDK4/6 based inhibitors, utilizing modified cells involving an E2F reporter system. Cancer cells are transduced with tdTomato fluorescent protein to specifically measure tumor size and an EGFP-firefly luciferase fusion gene under the control of E2F transcriptional response elements to measure pathway activity. Cells are then appropriately treated with a compound of interest and the amount of tdTomato can be compared to the firefly luciferase activity therein. By comparing the amount of tdTomato to the amount of firefly luciferase expression, the results of inhibition can be quantified.

A further embodiment is a method for screening novel compounds for inhibitory properties on E2F activity comprising applying a compound of interest to modified E2F reporter cells, comparing the amount of tdTomato expression to the amount of firefly luciferase activity in the cells and quantifying the results of the inhibition of the compound such as a CDK4/6 inhibitor.

A further method is a method for testing inhibitory compounds with regard to efficacy for inhibition of the E2F pathway through establishment of a cell-based E2F reporter system that provides for quantitative analysis of pathway inhibition in vivo and in vitro. The method comprising establishing a cell-based E2F reporter system as described herein, wherein the method comprises determining the efficacy of an inhibitor to block E2F signaling in melanoma cells in a non-invasive manner, and provides that the amount of inhibition can be quantified by comparing the amount of expressed firefly luciferase as compared to the amount of expressed tdTomato.

A further embodiment is directed to a high-throughput in vitro screening method, comprising: loading reporter cells comprising an E2F response element-EGFP-firefly luciferase construct onto a screening plate, mixing at least one compound of interest in a test vehicle, administering to at least one cell on said screening plate the compound of interest, and administering to at least a second cell, the test vehicle, incubating said cells for a predetermined amount of time, after incubating, comparing the amount of firefly luciferase activity to the level of actin/tdTomato activity between the compound of interest and of the test vehicle, and quantifying the level of block for the cells treated with the compound of interest, by normalizing firefly luciferase activity to tdTomato activity/actin levels.

A further embodiment is directed to a high-throughput screening kit comprising a plate comprising a plurality of wells, and disposed within said wells are a predetermined number of transduced cells comprising an E2F response element-EGFP-firefly luciferase construct, wherein the cells within a well can be administered a compound of interest, wherein the compound and cells are incubated for a predetermined amount of time. Intracellular luciferase is analyzed by lysing the cells and a luciferase substrate, luciferin is added to the cell lysates and luminescence signal can be measured using a luminometer. tdTomato fluorescent protein can be measured using fluorometer or actin levels measured using a western blot. Pathway activity, which identifies the percent of block the compound of interest towards the E2F signaling pathway can then be quantified by normalizing firefly luciferase activity to tdTomato activity/actin levels.

A further embodiment comprises a system for determining whether a compound is efficacious for inhibiting CDK4/6 in a melanoma cell comprising:
 a. a transduced cell with tdTomato fluorescent protein and EGFP-firefly luciferase fusion gene under the control of E2F transcriptional response element;
 b. applying a compound for inhibition of the CDK4/6 pathway; and
 c. comparing the fluorescence of tdTomato to firefly luciferase activity to quantify the amount of inhibition of the pathway.

A further embodiment is directed to a method for determining block of the E2F pathway comprising; generating a cell line comprising (1), E2F response elements-EGFP-firefly luciferase construct and (2), tdTomato fluorescent protein; implanting said cells subcutaneously or intradermally into an immunodeficient nude mouse, treating said mouse with compound of interest for a certain amount of time, measuring the amount of firefly luciferase by intraperitoneal injection of luciferin in the mouse and subsequent utilization of an IVIS in vivo imaging system. In parallel, fluorescence intensity of tdTomato within the tumor is imaged. By normalizing the firefly luciferase activity to tdTomato activity or tumor volume, the in vivo method can be used to test and determine the efficacy of a compound of interest for block of the E2F pathway in a temporal manner, and also to monitor for resistance of the drug. Resistance to the compound of interest can be tested by monitoring firefly luciferase activity and tdTomato activity in a temporal manner and looking for an increase in the value of firefly luciferase activity normalized to tdTomato fluorescence. Typically, resistance is evident through a significant increase in the value of firefly luciferase activity normalized to tdTomato fluorescence, such as a greater than 10% increase in a day, but may include a 25%, 50%, 100% or more increase over a period of between about one and seven days.

A method for determining the level of block of a compound of interest comprising; performing a first in vitro screen of said compound, comprising administering said compound to a reporter cell model, incubating said cell and compound, measuring luciferase and tdTomato fluorescence in said cell after said incubation period and determining the level of block; performing a second screen, comprising of an in vivo screen of said compound, comprising implanting said cells subcutaneously or intradermally into an immunodeficient nude mouse, treating said mouse with compound of interest for a certain amount of time, measuring the amount of firefly luciferase and tdTomato fluorescence by imaging the mouse utilizing an IVIS in vivo imaging system and comparing the intensity of firefly luciferase to the intensity of tdTomato fluorescence.

The embodiments described above can be suitably utilized with a cancer cell. In certain preferred embodiments, it is advantageous to utilize a melanoma cell as the cancer cell, however, other embodiments may suitably use a cancer cell including, a non-limiting list including a cell from a cancer of breast, mouth, lung, pancreas, esophageal, uveal, colon, prostate, or other cancer of interest. The cancer cells can be advantageously modified with the reporter mechanism as described herein, whereby compounds of interest can be suitably tested against said cells for efficacy of said compound.

DETAILED DESCRIPTION OF THE PREFERRED EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used here, the term "about" refers to within 10% of a stated number.

Aberrant cell cycle progression is a hallmark feature of cancer. The cell cycle consists of distinct phases: G0 (quiescence), G1 (pre-DNA synthesis), S (DNA synthesis), G2 (pre-division) and M (cell division) and is tightly regulated by a network of cyclin dependent kinases (CDKs), cyclins and CDK inhibitors (CDKI). Positive interaction between CDKs and cyclins drives cell cycle progression, whereas CDKIs act as a brake by negatively regulating CDK activity. Commitment to the cell cycle occurs in G1 phase and involves CDK4/6 in association with D-type cyclins contributing to the inactivation of the tumor suppressor, retinoblastoma (RB). This uncouples RB from E2F transcription factors, which allows E2F to drive the transcription of E2F-regulated genes. Although interphase CDKs are targetable, early generation CDK inhibitors (e.g. flavopiridol) were non-selective and showed limited therapeutic value in melanoma patients.

Inhibitors of cell cycle components, CDK4/6, are currently being tested in clinic with significant advances being made in breast cancer research. The response of cancer cells to CDK4/6 inhibitors relies on the presence of tumor suppressor RB that binds to and inhibits E2F from transcribing its target genes. It is expected based on studies that effective inhibition of E2F will be correlated with positive clinical responses. The recent FDA approval of an orally available, highly selective inhibitor of CDK4/6, palbociclib (IBRANCE/PD-0332991) in post-menopausal estrogen receptor (ER)-positive/HER2-negative breast cancer has rekindled interest in targeting cell cycle progression in cancer. Palbociclib also showed clinical activity in mantle cell lymphoma with oncogenic t(11;14)(q13;q32) translocation resulting in the aberrant expression of cyclin D1.

Figure 1:
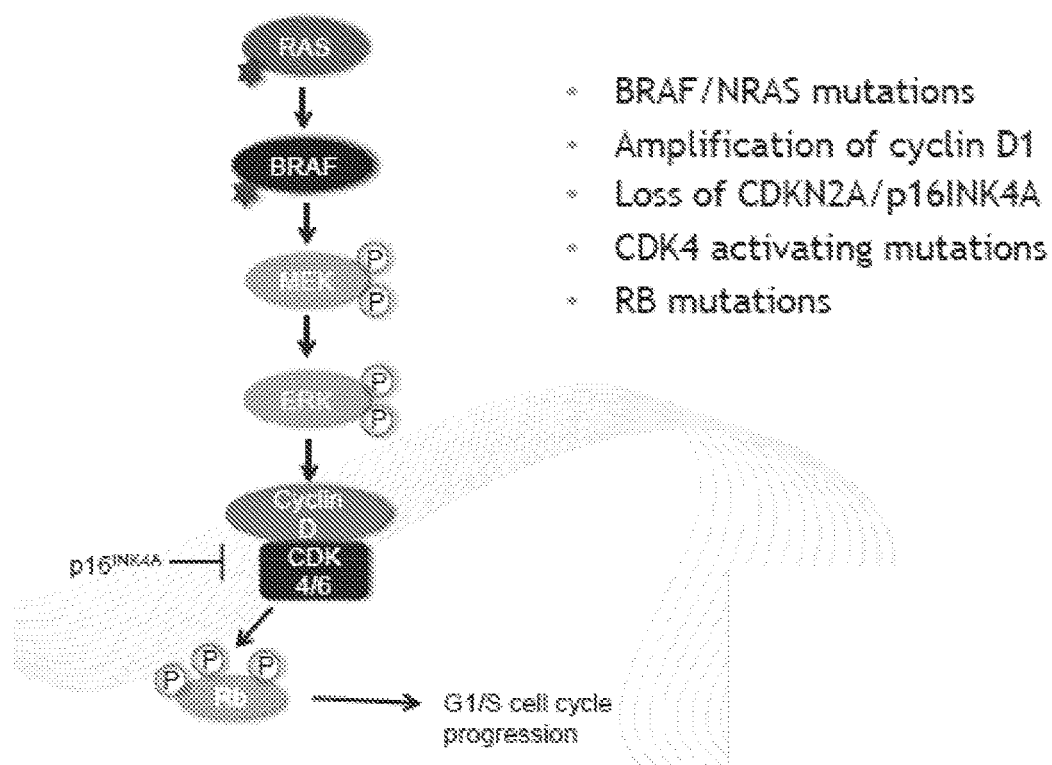
FIG. 1 depicts an overview of the CDK4/6 pathway in melanoma.

In melanoma, multiple mechanisms drive aberrant progression through the cell cycle leading to uncontrolled proliferation; thus, providing a rationale for therapeutically targeting CDK4/6. Mutations in BRAF (~50% frequency) and in NRAS (15-20%) activate the MEK-ERK1/2 pathway, which upregulates cyclin D1. Inactivation of RB1 also occurs through CDK4 mutation, loss of functional CDKI proteins such as p16INK4A and p14ARF, and, to a lesser degree, loss of RB1 itself. In view of FIG. 1, an overview of the CDK4/6 pathway in melanoma is depicted. FIG. 1 identifies the pathway beginning with RAS, RAF, MEK, ERK, Cyclin D, CDK 4/6, wherein activated CDK4/6 can phosphorylate tumor suppressor, RB leading to the inactivation of RB.

Figure 2:
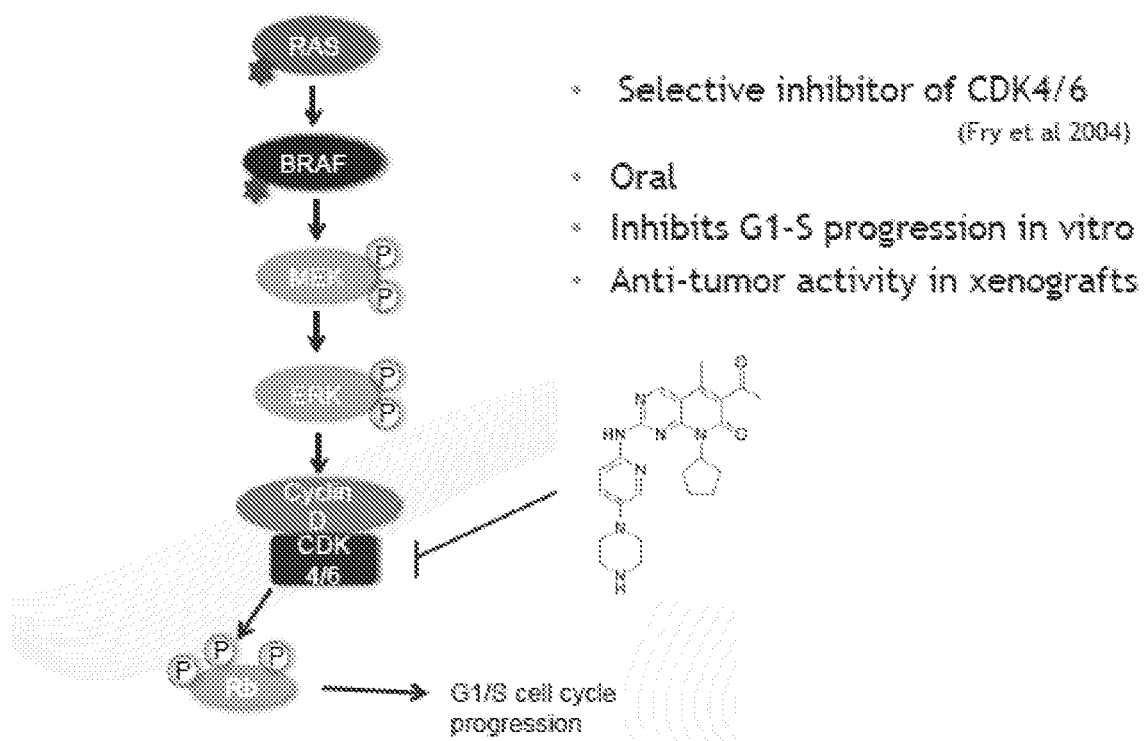
FIG. 2 depicts an overview of the effects of CDK4/6 inhibitor (Palbociclib) in vitro.

This knowledge has led to studies analyzing the effects of targeting CDK4/6 in melanoma (FIG. 2). Indeed, FIG. 2, depicts a flow-chart of palbociclib, a CDK4/6 selective inhibitor, wherein Palbociclib inhibits G1-S progression in vitro and provides for anti-tumor activity in xenografts. In vitro studies show that loss of functional p16INK4A through deletion, hyper methylation or mutation in melanoma cells correlated with palbociclib sensitivity. Mutant NRAS extinction in an inducible NRAS genetically engineered mouse (GEM) model decreased cell cycle progression via effects on the expression of CDK4 and increased apoptosis via inhibition of the MEK-ERK1/2 pathway. Furthermore, simultaneous targeting of MEK and CDK4 inhibited tumor growth of mutant NRAS SB-2 cell xenografts.

Given the promising development of cell cycle intervention in breast cancer, mantle cell lymphoma, and melanoma, it is expected that significant development of old or new compounds will progress, wherein it will be necessary to determine a response to CDK4/6 inhibitors alone and in combination with other clinically relevant targeted agents for not just these cancers, but any number of cancer types. This is important to identify subgroups that will likely benefit from CDK4/6 inhibitors and to assist in patient selection in clinical studies. Therefore, a reporter system that can provide for in vitro and/or in vivo screening protocols providing a new opportunity to test and quantify efficacy of compounds of interest, and also includes the opportunity to determine whether certain cells have resistance to the compounds of interest, is of great value.

Applicants have created an E2F-dependent luciferase reporter cell line to enable temporal quantification of the effects of CDK4/6 inhibitor based treatments in a quantitative, non-invasive, and tumor-selective manner. In this reporter system, hyper-phosphorylation of RB1 leads to the uncoupling of E2F and subsequent E2F-mediated induction of firefly luciferase activity. 1205Lu cells were chosen based on their ability to form tumors in vivo and their utility in a previously developed ERK1/2 reporter system. However, no current method exists to quantify E2F activity in melanoma cells in real-time known methods and current assays have the ability to detect inhibition, but there is no way to quantifying the amount of inhibition in such cells by the particular inhibiting agent. Therefore, when comparing the efficacy of one agent over another, there is a need for the ability to quantify the results to appropriately determine the efficacy of a compound.

The cells described herein, and the methods of using the same, provide for the ability to quantify and compare the efficacy of compounds that inhibit the E2F pathway, including inhibition of CDK4/6 activity. Modified cells include a reporter system comprising E2F response elements-EGFP-firefly luciferase construct and a tdTomato fluorescent protein that express a reporter that allows compounds to be screened against a control, to test for compounds that alter the activity of the E2F pathway. The reporter system, unlike currently known systems, provides a mechanism to not only test for efficacy, but to quantify the same by comparing the level of tdTomato to the luciferase and quantifying the same. Indeed, the ability to quantify the efficacy of the inhibition is performed by comparing the luciferase activity to tdTomato activity, which is tumor selective and measures tumor size.

In preferred embodiments, the novel reporter system is a transduced melanoma cell having transduced an EGFP-firefly luciferase fusion gene, under the control of E2F transcriptional response elements. Applicants transduced mutant BRAF melanoma cells 1205Lu and mutant NRAS melanoma cells, WM1366 to express EGFP-firefly luciferase fusion gene under the control of E2F response elements.—Accordingly, methods of the present disclosure take the transduced melanoma cell and apply an inhibitory compound. The cells are then incubated for a period of time and then firefly luciferase activity is measured. The amount of inhibition of the CDK4/6 pathway can be determined by comparing the amount of firefly luciferase expression to the amount of expression of tdTomato. Multiple genotypically distinct melanoma models can be generated.

In this reporter system, hyper-phosphorylation of RB1 leads to the uncoupling of E2F and E2F-mediated induction of firefly luciferase activity. 1205Lu cells were chosen based on their ability to form tumors in vivo and their utility in a previously developed ERK1/2 reporter system. Tumor cells were also transduced with tdTomato fluorescent protein to selectively monitor tumor growth. The tdTomato is expressed in every cell thus measurement of its activity measures the quantity of cells present, wherein the Firefly luciferase activity measures the amount of E2F that is available to bind to its response elements in the reporter construct thus driving the signaling pathway. By comparing the two measurements, the reporter system enables one to quantify the amount of block of the compound of interest.

Accordingly, a method of the present disclosure involves utilizing modified cells involving a modified E2F reporter system to monitor the efficacy of CDK4/6 inhibitor based therapies both in vitro and in vivo. Tumor cells are transduced with tdTomato fluorescent protein and an EGFP-firefly luciferase fusion gene under the control of E2F transcriptional response elements. In vitro, cells are then appropriately treated with multiple compounds of interest and firefly luciferase activity can be measured and normalized to the amount of tdTomato activity/actin levels in the cells. In vivo, reporter cells are injected in immunodeficient nude mice and when the tumors arise, the mice are treated with compounds of interest that show effective inhibition of luciferase activity in vitro. Firefly luciferase activity can imaged and quantified and then normalized to tdTomato activity in the tumors. By normalizing the amount of firefly luciferase activity to tdTomato activity, the results of inhibition in the tumor can be quantified.

Therefore, an embodiment of the invention is the ability to quantify the amount of inhibition of a particular compound to inhibit reporter activity in these cell models. To make this quantification, one compares Firefly luciferase activity to tdTomato. The tdTomato fluorescence is altered based on tumor size, whereas the firefly luciferase activity is modified based on the inhibition of the particular compound on the signaling pathway. Thus, effective inhibition of the pathway by a particular compound can be visualized by quantifying luciferase activity normalized to tdTomato fluorescence. Cells that are resistant to a particular compound will maintain high firefly luciferase/pathway activity.

The reporter cells described herein can be any cancer cell type. Indeed, by using the embodiments described herein, different types of cancer cells can be transduced with the E2F dependent reporter construct to test different clinically relevant compounds for block of the E2F pathway. Therefore, a preferred embodiment is directed to a method for generating a reporter cell line, comprising identifying a cancer cell, transducing the cancer cell with tdTomato fluorescent protein to specifically measure tumor size and an EGFP-firefly luciferase fusion gene under the control of E2F transcriptional response elements to measure pathway activity. Cells are then appropriately treated with a compound of interest, incubated, and imaged, and the amount of tdTomato can be compared to the firefly luciferase activity therein in either in vitro or in vivo screening methods. By comparing the amount of tdTomato to the amount of firefly luciferase expression, the results of inhibition can be quantified.

In certain embodiments, a kit may also be suitable comprising (1) E2F response elements-EGFP-Firefly luciferase plasmid/lentivirus, and (2) tdTomato fluorescent protein plasmid/lentivirus. Wherein, the components can be utilized in conjunction with a cancer cell to generate a reporter cell line of interest, and test compounds of interest under the methods as described herein. In preferred embodiments, applicants' specific reporter system utilizes firefly luciferase. However, other suitable luciferase reporters e.g. *Renilla* luciferase or fluorescent proteins e.g. mCherry may be interchangeably utilized to optimize the sensitivity of the system for the particular cell type.

A further method is a method for screening compounds for inhibitory properties on E2F melanoma cells comprising applying two or more compounds of interest to a modified reporter cell, comparing the amount of tdTomato expression to the amount of firefly luciferase expression in the cell and quantifying the results of the inhibition of the compound. Therefore, a method for screening compounds of interest for inhibitory properties on E2F reporter melanoma cells, provides for the ability to examine the efficacy of multiple compounds onto a cell at once. Furthermore, in a high-throughput screen, dozens of wells can be utilized at once to test one or more compounds per well, to increase the rate of testing of compounds. These screens provide an opportunity to identify compounds that show greatest activity to inhibit E2F pathway such as upstream inhibitors of the E2F pathway e.g. inhibitors of the MAP Kinase pathway (MEK inhibitors and ERK inhibitors). Compounds that are particularly effective in the screen can then be further tested in mouse xenograft models.

A further embodiment is directed to a method for screening compounds using an in vitro and in vivo screening process. The method comprises a first in vitro screening process to identify compounds that have a block of 50% or greater than control. These compounds meeting the limitation of 50% block can then be further tested in vivo, wherein the reporter cells are injected into an immunodeficient nude mice and tumors are allowed to grow. When the tumors arise, the mice are treated and pathway/luciferase activity is imaged and quantified along with tdTomato fluorescent protein activity. Normalized firefly luciferase activity to tdTomato activity can be quantified and represents the amount of pathway inhibition when compared to control mice. The 50% block limitation can be modified from a percent of about 10% to about 100%, in order to have more or less restrictive screening process.

A further advantage of the system is as a method for testing inhibitory compounds in vivo in the same tumor. This permits temporal analysis of the same tumor. Pathway activity can be plotted against time as the one tumor is monitored in the same mouse to either regress or acquire resistance.

A further advantage is the use of the reporter to determine effective scheduling and dosing of compounds before the drug is moved to the clinic. Combination therapy can induce severe toxicities in patients. Utilizing the reporter system, drug concentrations can be optimized by testing various drug concentrations and combinations that results in the highest inhibition on pathway activity with the least present side effects/toxicities. Similarly, scheduling of drugs such as a three week ON and 1 week off schedule versus other schedules can also be tested by looking at inhibition of pathway activity. Reactivation of the pathway also corresponds with an actively proliferating tumor and subsequent resistance to drugs.

The reporter construct may also be transfected into different cancer cell lines as well as individual patient derived tumors. In patient derived xenograft reporter models, a tumor is extracted from a patient. The tumor is homogenized to single cell cultures and subsequently, the E2F reporter construct and tdTomato fluorescent protein is transfected into the tumor cells. After transfection the cells are xenografted into mice and the mice are treated with test compounds. Firefly luciferase activity normalized to tdTomato activity measures the efficacy of the test compound with percent inhibition of E2F activity as the output. Patient derived xenografts are clinically relevant unlike established human cell lines as they are more heterogeneous and can allow for individualized precision medicine.

Indeed, precision medical treatments may allow for an individual patient cancer cell to be systematically be tested with hundreds of potential compounds of interest before determining a precise individual compound or cocktail combination of compounds that provides for the single best treatment for the individual and their particular cancer cell/form. Because of the ability to test these quickly in mouse models as well as in in vitro models, such testing may allow for precision medicine and individualized care.

EXAMPLES

The following non-limiting examples are provided to give examples of the manner and mechanism for creating the reporter cells, testing the cells in vitro and in vivo and providing examples of methods for testing and using the reporter cells described herein.

Applicants using the reporter system described herein tested and determined that concurrent targeting of CDK4/6 and MEK resulted in enhanced deleterious effects in cell viability and apoptosis in both BRAF and NRAS mutant melanoma cells. Furthermore, mechanistic investigation uncovered one potential mediator of response to CDK4/6 plus MEK inhibitors as survivin, a known survival factor in melanoma. On the basis of these findings, the in vitro results were corroborated to demonstrate significant tumor regressions in vivo with simultaneous CDK4/6 and MEK inhibition compared to single agents alone. The efficacy of the combination was demonstrated using the in vivo E2F activity reporter melanoma xenograft system to temporally quantitate the effect of the inhibitors and allow for the quantitative and temporal analysis of pathway reactivation during acquired resistance.

Figure 3A:
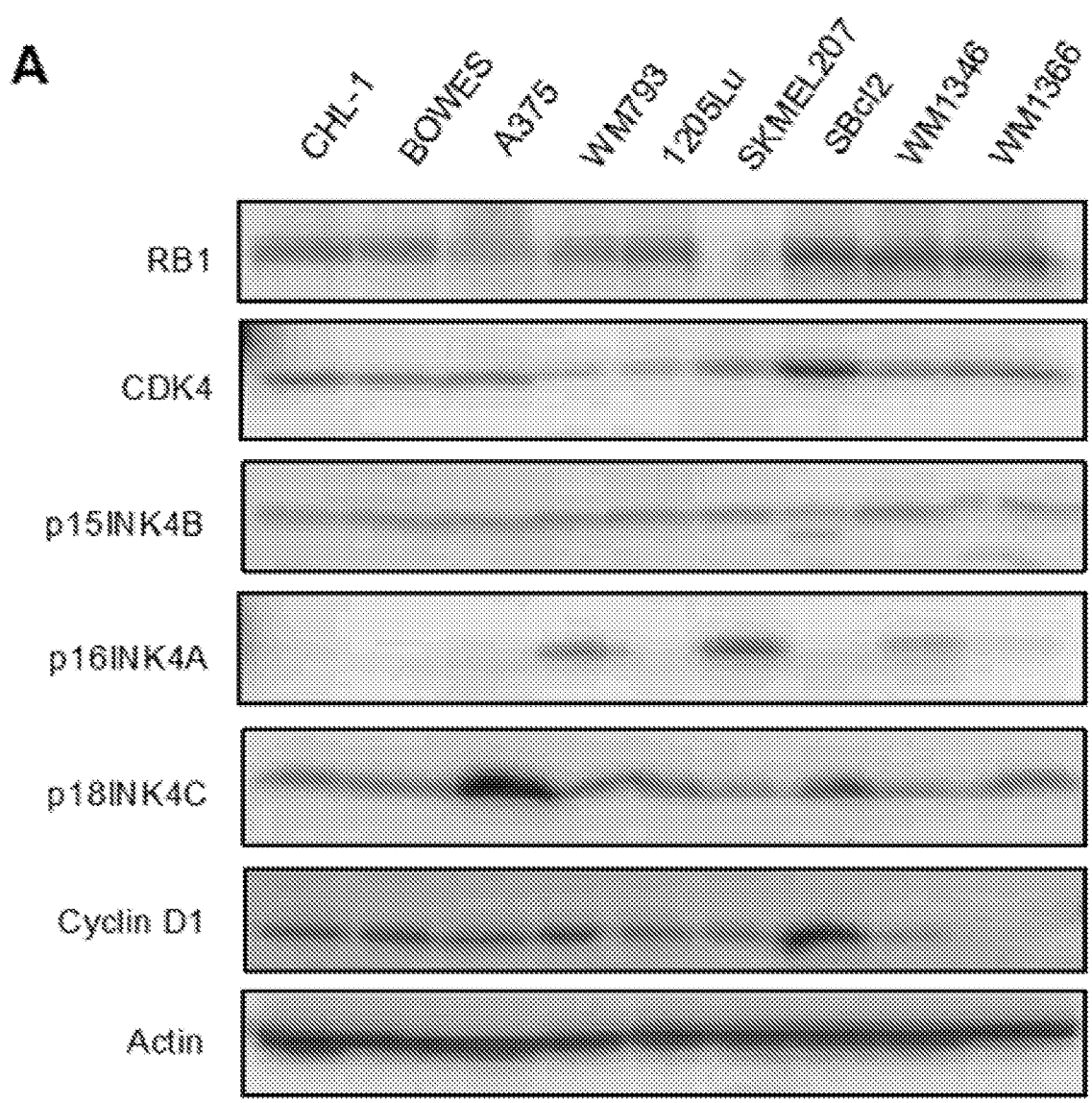
FIGS. 3A-3E depict cytostatic effects of palbociclib in melanoma.
Figure 3B:
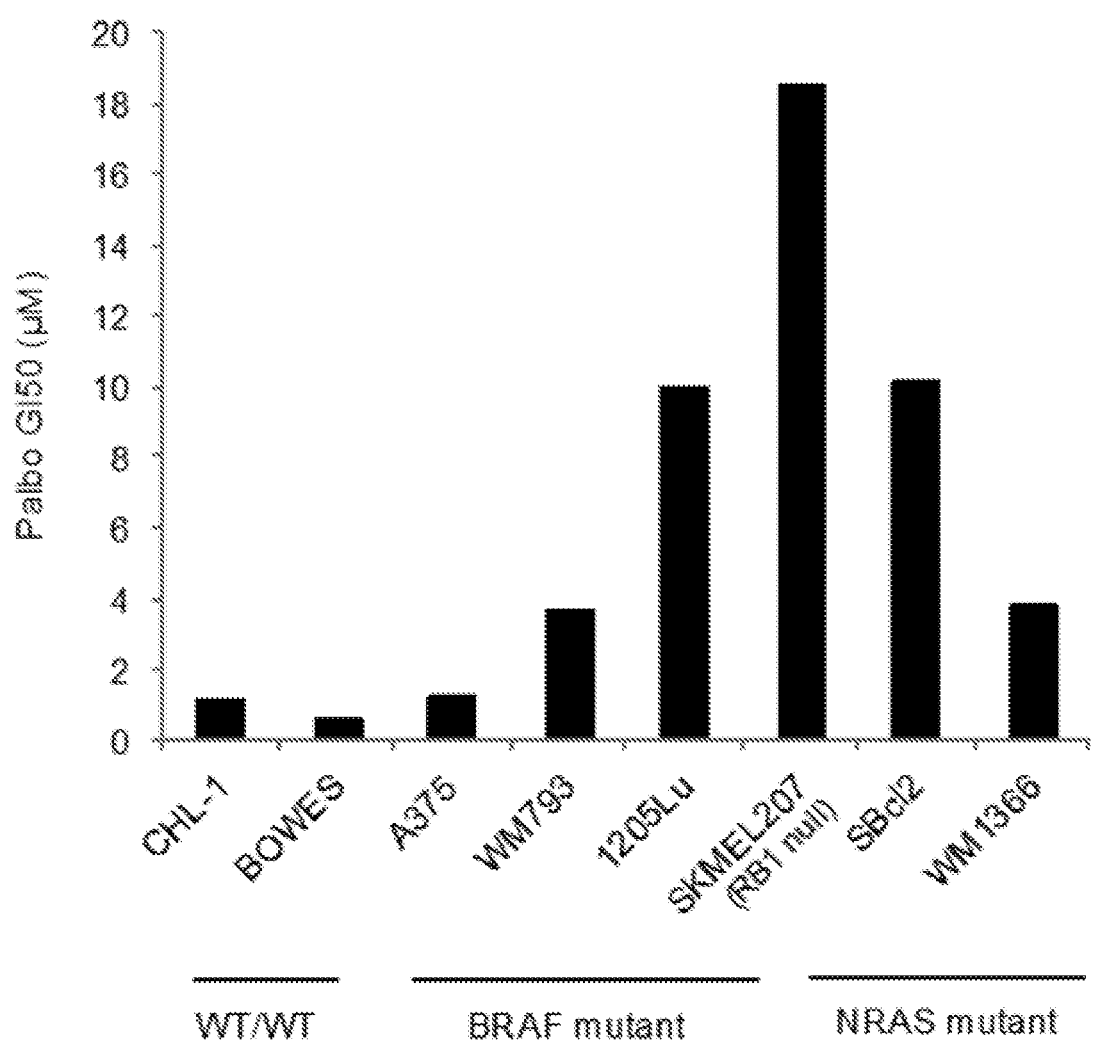
Figure 3C:
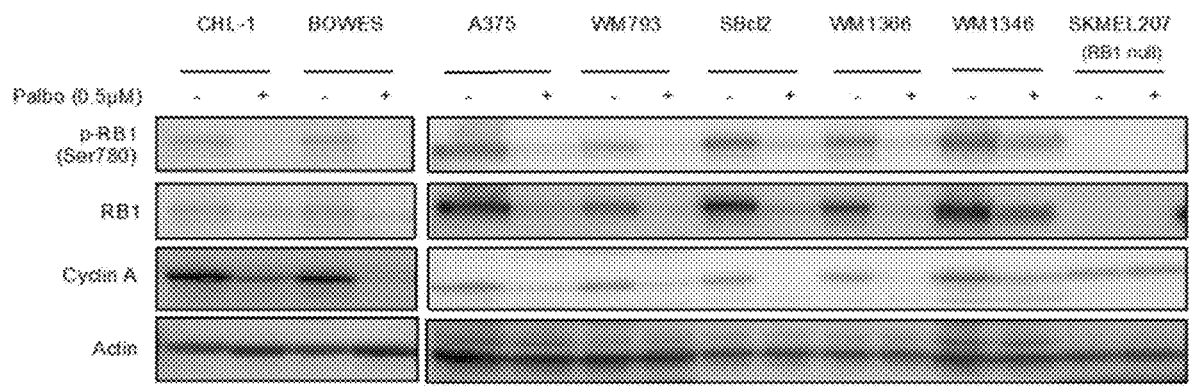
Figure 3D:
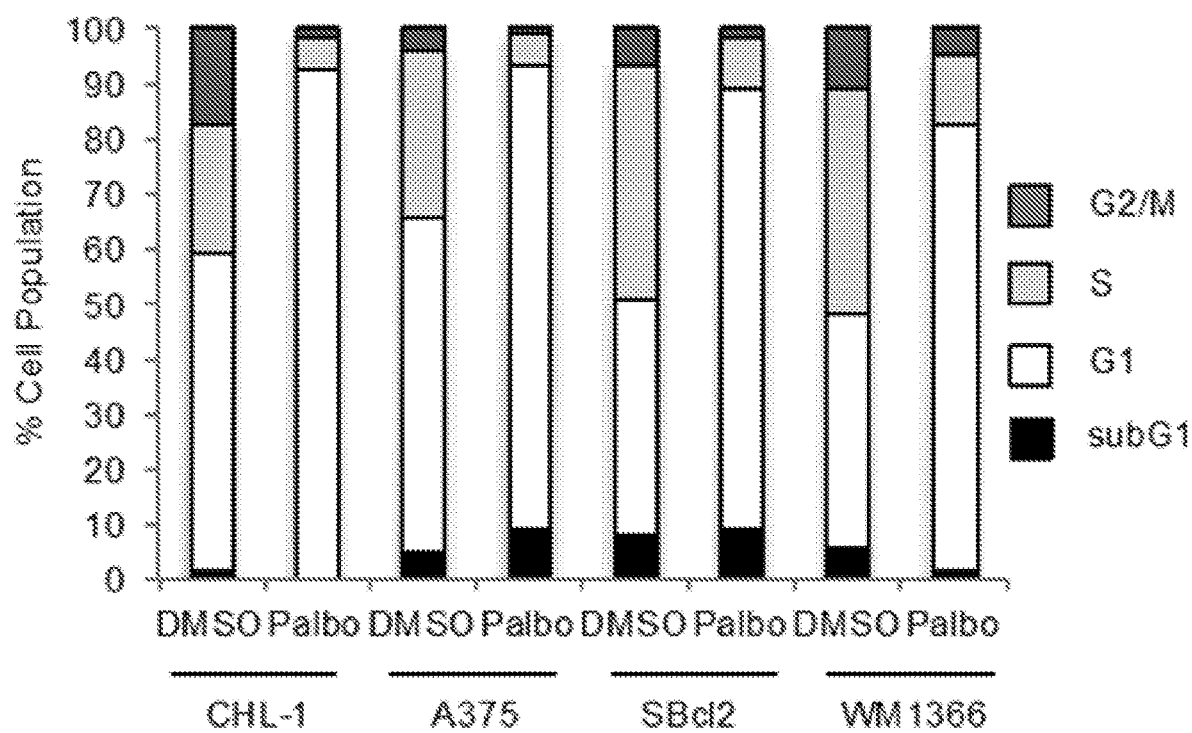

To determine the sensitivity of melanoma cells to CDK4/6 inhibition, the response of a genetically diverse panel of melanoma cell lines to palbociclib was examined (FIG. 3A). FIGS. 3A-3D depicts differential response of melanoma cells to CDK4/6 inhibition. FIG. 3A depicts Western blot of potential biomarkers of response to palbociclib in a panel of melanoma cell lines. FIG. 3B depicts sensitivity of melanoma cells to palbociclib. GI50 values were generated from dose-dependent curves from MTT cell viability assays. Each bar represents the average of three independent experiments. FIG. 3C depicts palbociclib treated melanoma cells were analyzed by Western blotting for RB1 phosphorylation and expression of RB1 and cyclin A. FIG. 3D depicts that melanoma cells were treated with palbociclib for 24 hours and analyzed by PI staining. The relative distribution of cells in the subG1, G1, S and G2M phases of the cell cycle is shown. E. Mice bearing 1205Lu xenografts were treated with control chow (n=4) or palbociclib chow (n=8). (Error bars represent SEM, *p<0.05).

As depicted in FIG. 3, cells were treated with increasing concentrations of palbociclib in order to determine the GI50 for each cell line. The response of melanoma cells to palbociclib was heterogeneous with the wild-type (WT) BRAF and NRAS cell lines, CHL-1 and BOWES, showing the highest sensitivity (FIG. 3B). By contrast, the mutant BRAF and RB1 null cell line, SKMEL207, showed the lowest sensitivity. No clear correlation was observed between CDKN2A mutational status or INK4 family protein expression and the response to palbociclib within the panel (FIGS. 3A and 3B). For example, SBcl2 cells are p16INK4A-deficient concurrent with high CDK4 and cyclin D1 expression but were relatively resistant to CDK4/6 inhibition (FIG. 3A, 3B). Phosphorylation of RB1 and cyclin A2 expression were decreased within 24 hours of exposure to palbociclib with effects more evident at low concentrations (0.05 µM) in the more sensitive cell lines.

Figure 3E:
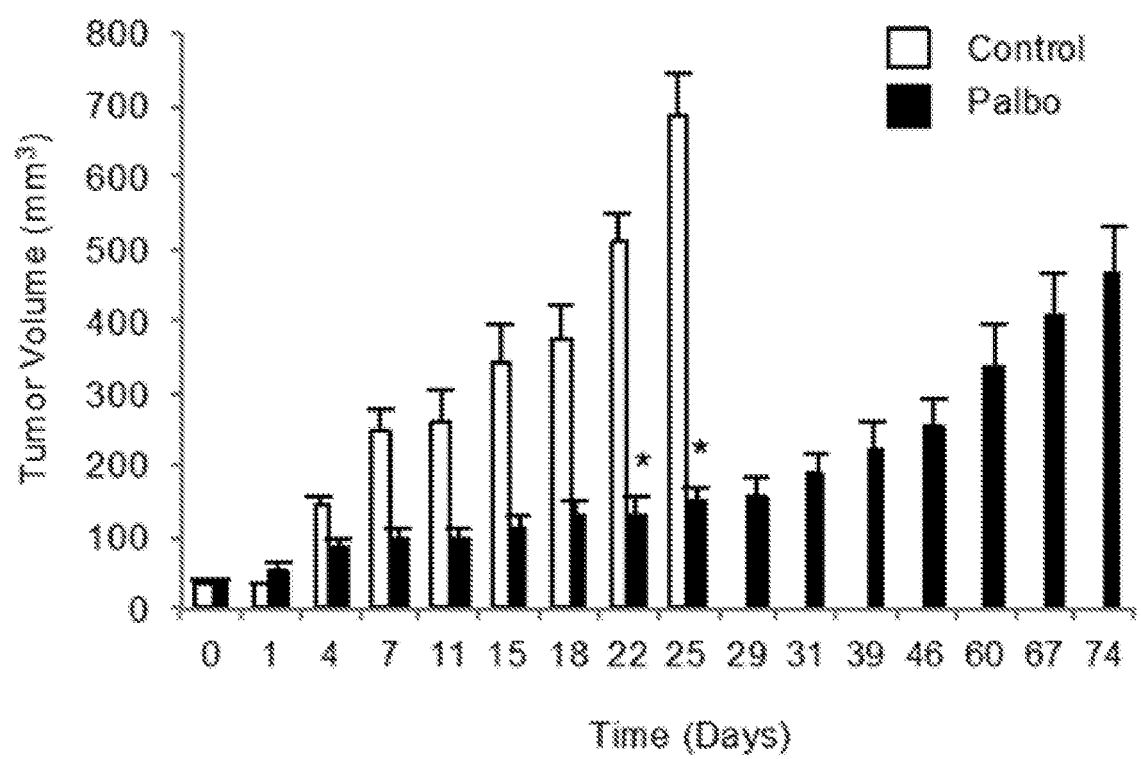

Irrespective of the GI50, acute treatment with 0.5 µM palbociclib resulted in decreased phosphorylation/expression of RB1 and cyclin A2 in all cell lines except RB1-null, SKMEL207 (FIG. 3C). To further characterize the cellular response to palbociclib as a single agent, a panel of cells was treated with palbociclib and performed propidium iodide (PI)-based cell cycle analysis. Twenty-four hour treatment of palbociclib induced a G0/G1 cell cycle arrest but not cell death represented by a lack of subG1 accumulation (FIG. 3D). Furthermore, palbociclib as a single agent initially suppressed 1205Lu tumor growth in vivo but progressive growth ensued (FIG. 3E). Taken together, these results show that the response of melanoma cells to palbociclib is heterogeneous, may not clearly stratify to any one genotype, and leads to cytostatic effects but neither cell death nor tumor regression.

CDK4/6 and MEK Inhibitors Synergize to Inhibit the Growth of BRAF- and NRAS-Mutant Melanoma Cell Lines.

Due to the inability of single agent palbociclib to induce cell death, whether CDK4/6 targeting sensitized melanoma cells to MEK targeting is explored. Treatment with the MEK inhibitor, trametinib, blocked the growth of all cell lines tested although RB1-deficient mutant BRAF SKMEL207 cells displayed decreased sensitivity. Since the CDK4/6 plus MEK inhibitor combination represents a targeted inhibitor option that is applicable across all melanoma genotypes, cell lines were treated with palbociclib alone, trametinib alone or both inhibitors in combination over a fixed-ratio, 7-point concentration range for 96 hours. The combination of palbociclib and trametinib reduced the viability of BRAF and NRAS mutant cell lines compared to single agent treatments (FIG. 4A).

Figure 4A:
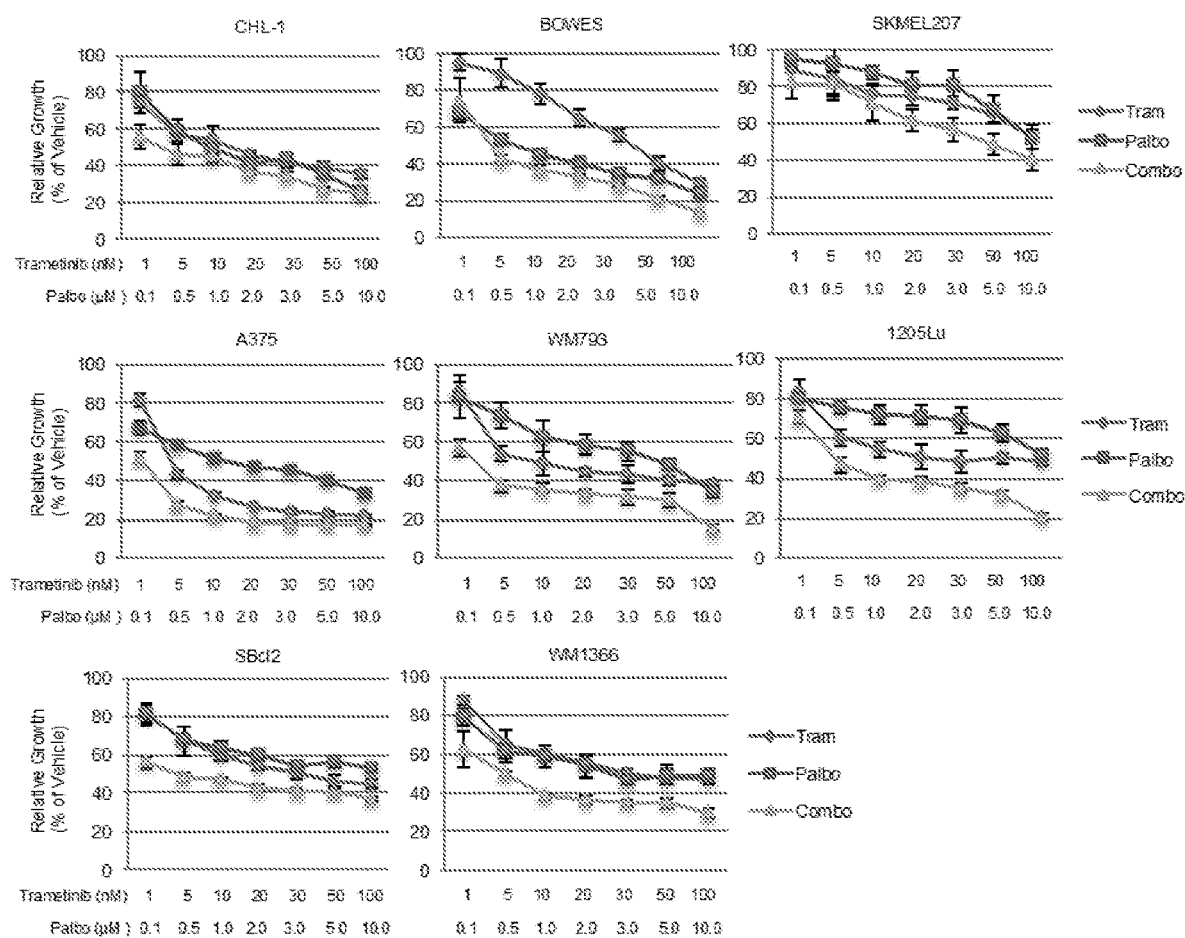
FIGS. 4A-4C depict enhanced effects of combined MEK and CDK4/6 inhibition in BRAF and NRAS mutant lines in vivo.
Figure 4B:
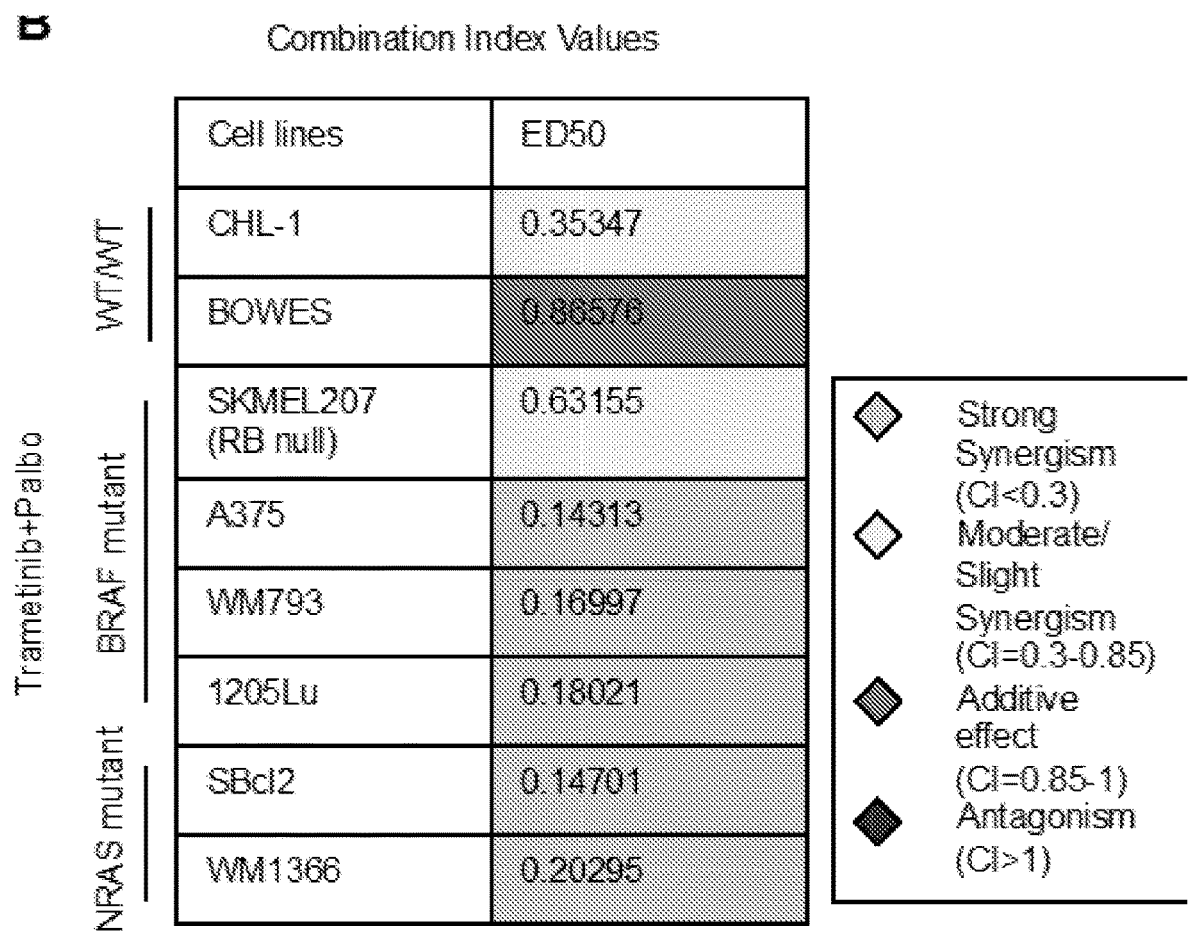
Figure 4C:
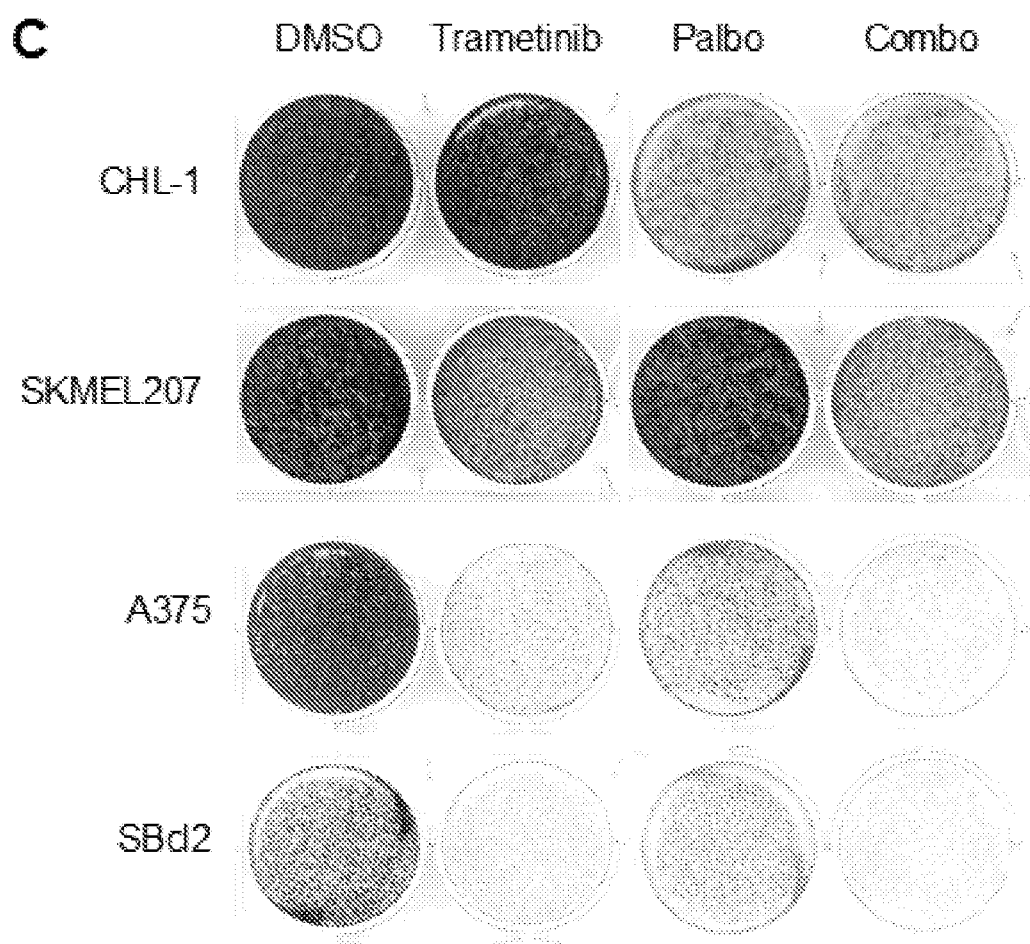

FIG. 4 depicts enhanced effects of combined MEK and CDK4/6 inhibition in BRAF and NRAS mutant lines in vitro. FIG. 4A depicts MTT cell viability assays of WT/WT, BRAF and NRAS mutant lines treated for four days with single agent (trametinib or palbociclib) or a fixed-ratio (1:100) combination (trametinib plus palbociclib) of both compounds (error bars represent SD). FIG. 4B depicts Calcusyn combination indices at median effective dose (ED50) generated from MTT assays in FIG. 4A. FIG. 4C depicts melanoma cells were plated at low density, treated with DMSO, trametinib (10 nM), palbociclib (1 mM) or the combination. After 1 week, cultures were stained with crystal violet.

On the other hand, there was only a modest effect of the combinatorial treatment on CHL-1 and BOWES cells (both WT BRAF/WT NRAS) and SKMEL207 (FIG. 4A). Calcusyn analysis revealed a strong synergism between the drug combination in mutant BRAF and mutant NRAS cells at median effective dose (ED50) but only moderate to slight synergism in CHL-1, BOWES and SKMEL207 cells (FIG. 4B). Effective long-term responses to the combinatorial treatment in A375 and SBcl2 cells were also confirmed by colony formation assay (FIG. 4C). Again, the palbociclib plus trametinib combination was less effective in CHL-1 and SKMEL207 cells compared to the other cell lines tested.

Down-Regulation of Survivin Associates with Response to CDK4/6 Plus MEK Inhibitor Combination.

Figure 5A:
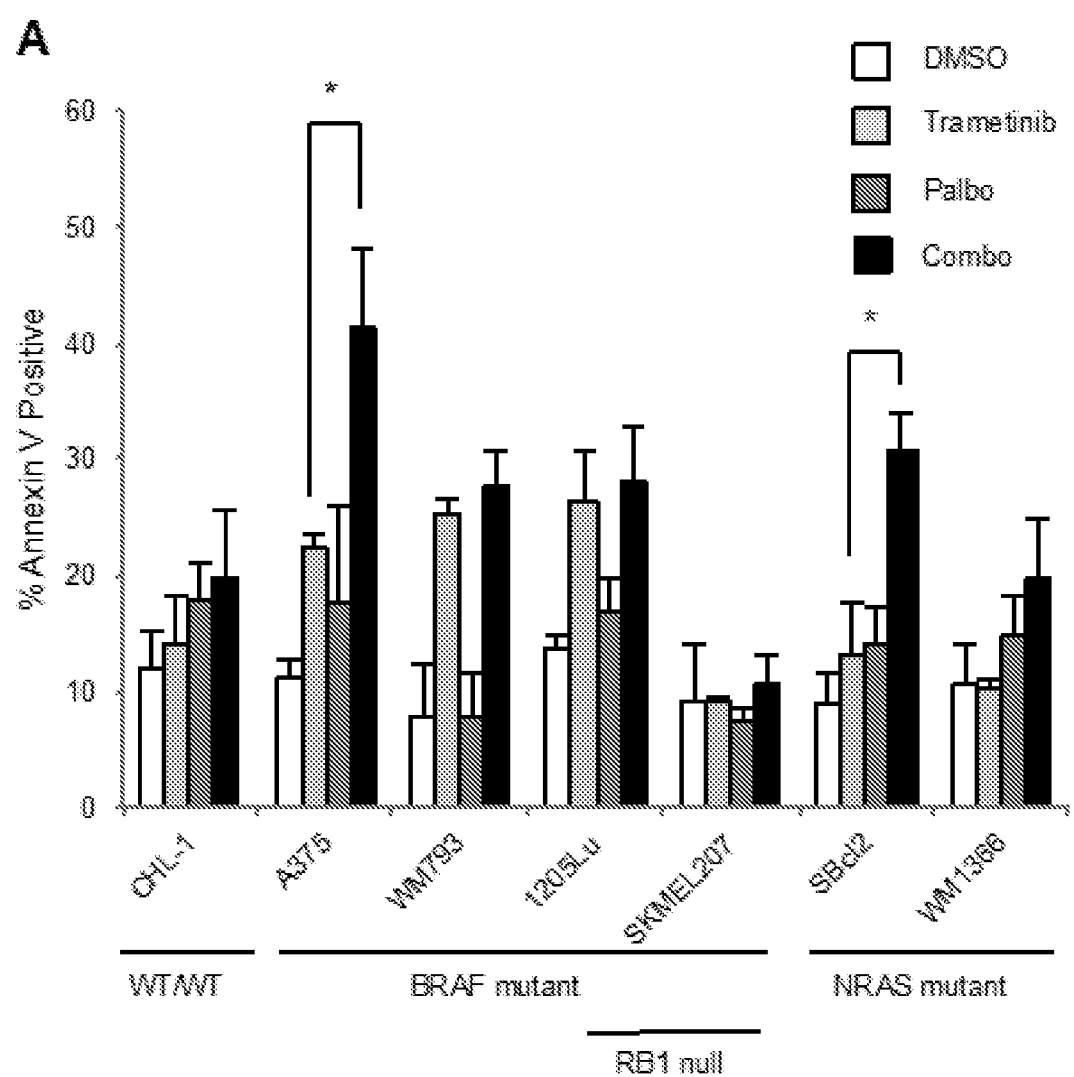
FIGS. 5A-5G depict sensitivity to combined CDK4/6 and MEK inhibition associated with survivin depletion in sensitive cells.
Figure 5B:
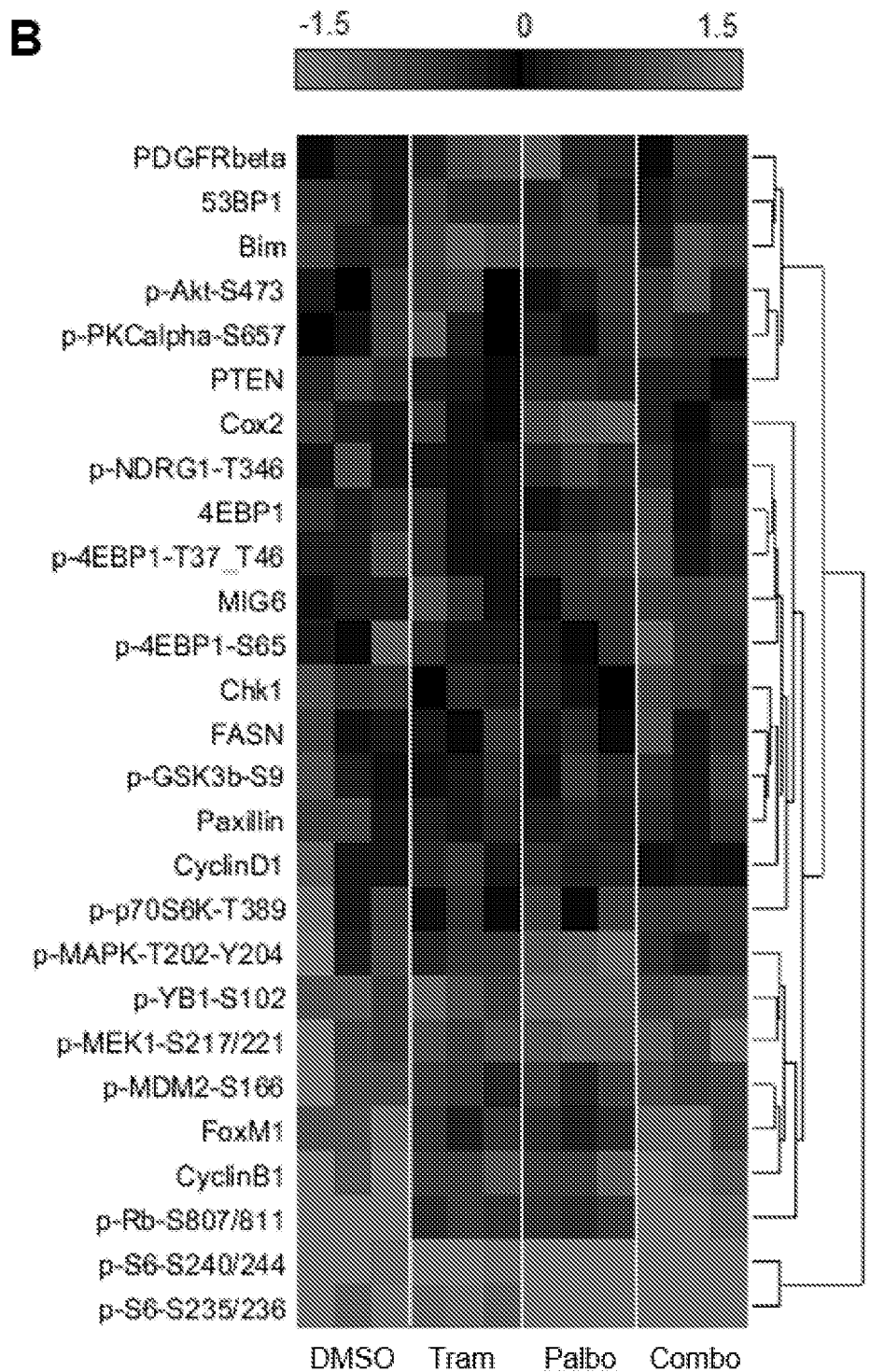

Therefore, a question arose as to whether the enhanced effect seen with the combination of CDK4/6 and MEK inhibition was due to apoptosis. An increased annexin V staining was observed when CDK4/6 and MEK were simultaneously inhibited in some cells (e.g. A375 and SBcl2) but not others (FIG. 5A). In WM793 and 1205Lu cells, MEK inhibition alone was sufficient to induce apoptosis. Consistent with these data, trametinib increased cleaved PARP levels in cell lines that showed enhanced effects to the combination.

FIG. 5 depicts sensitivity to combined CDK4/6 and MEK inhibition is associated with survivin depletion in sensitive cells. FIG. 5A. depicts a representative annexin V staining of human melanoma lines treated with trametinib (5 nM) and palbociclib (0.5 µM) treatment alone or a combination of both compounds for 48 hours (n=3, error bars=SD from triplicate samples, *p<0.05). FIG. 5B depicts A375 cells were treated with single agent or combination of trametinib (5 nM) and palbociclib (0.5 µM) for 24 hours. DMSO represents the control. Lysates were analyzed by RPPA. The heatmap shows the most significantly regulated proteins (p<0.01). FIG. 5C depicts that elevated levels of Bim-EL in trametinib and combo-treated lysates. FIG. 5D depicts that 1205Lu cells were transduced with silencing RNA to Bim in the presence or absence of trametinib (5 nM) and palbociclib (0.5 µM). Knockdown of Bim rescued apoptotic phenotype elicited by trametinib and palbociclib treatments. FIG. 5E depicts fold change in BIRC5/survivin regulation after 24 hours of treatment with indicated inhibitors. Two independent sets of tests were carried out and representative data is shown. FIG. 5F depicts western blotting analysis of survivin in cell lines in resistant (CHL-1, Bowes, SKMEL207) and sensitive (A375, WM793, 1205Lu, SBcl2, WM1346, WM1366) cell lines in basal state as well as following treatment with trametinib and/or palbociclib for 48 hours. FIG. 5G depicts NRAS mutant melanoma tumor explant treated with DMSO, trametinib (50 nM), palbociclib (0.5 mM) or the combination.

Figure 5C:
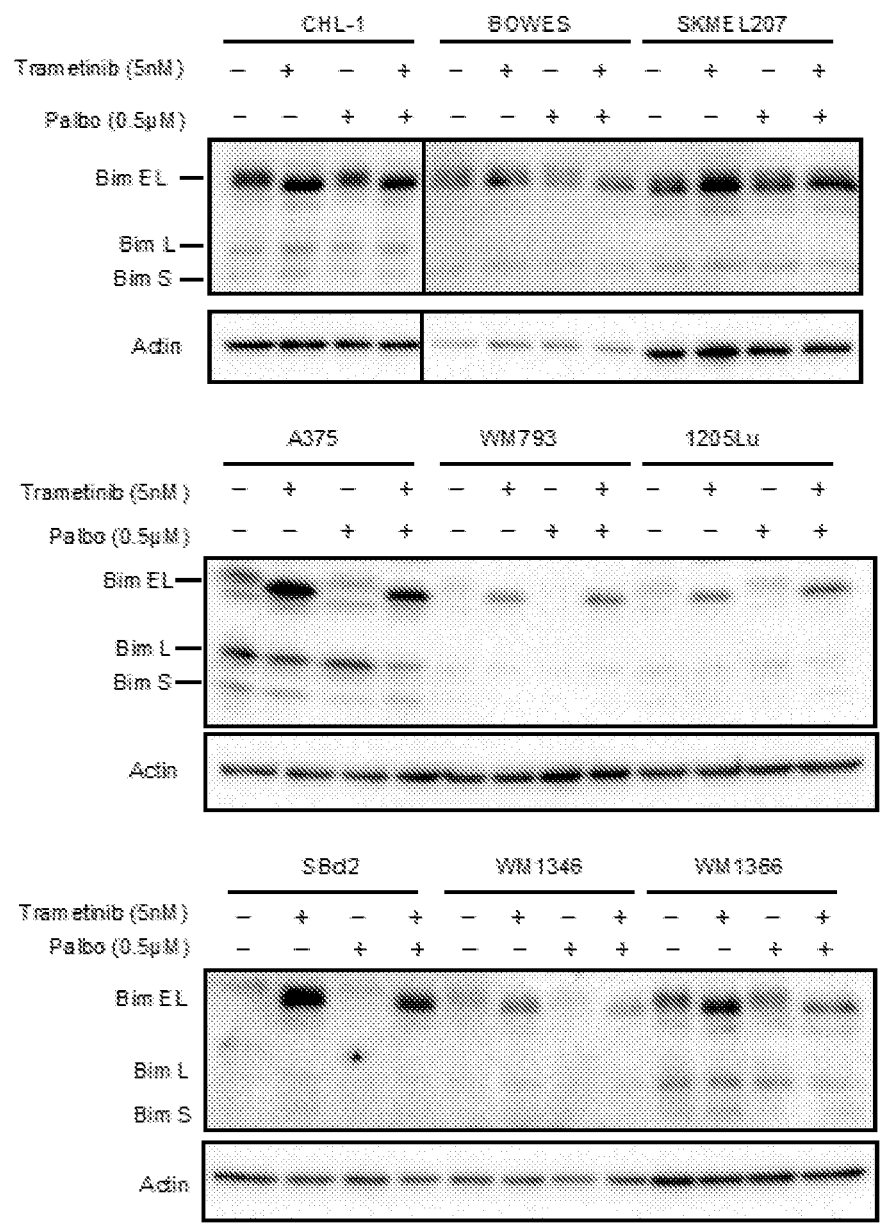
Figure 5D:
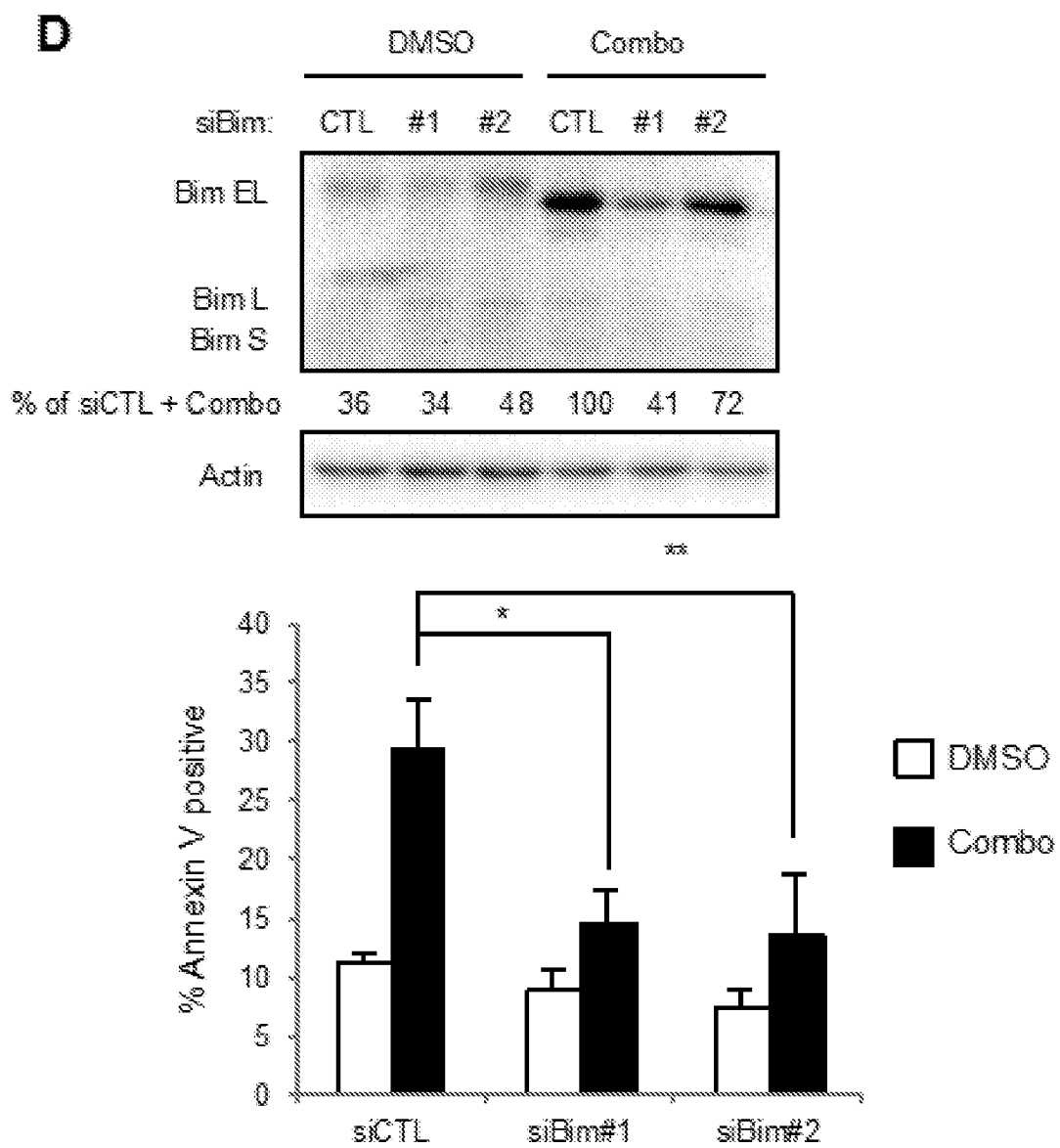

To analyze signaling proteins that may be perturbed by treatment of palbociclib and/or trametinib, RPPA profiling was performed on A375 cells treated with either single agent or with the combination. Phospho-RB1 and FOXM1, two established substrates of CDK4/6, were cooperatively repressed by co-inhibition of CDK4/6 and MEK. The pro-apoptotic protein, Bim-EL, was up-regulated by trametinib treatment but unaffected by palbociclib. Effects on Bim-EL levels in A375 cells was validated by Western blotting and also observed in combination inhibitor sensitive BRAF and NRAS mutant lines (FIG. 5C). Moderate changes were detected in Bim-EL levels in response to trametinib in the combination-resistant cell lines, CHL-1, BOWES and SKMEL207 (FIG. 5C). Finally, the requirement of Bim induction for the apoptosis induced by combination treatment in the sensitive, 1205Lu cell line, was tested. Knockdown of Bim in 1205Lu cells partially inhibited trametinib plus palbociclib-induced apoptosis as detected by reduced annexin V staining (FIG. 5D).

Figure 5E:
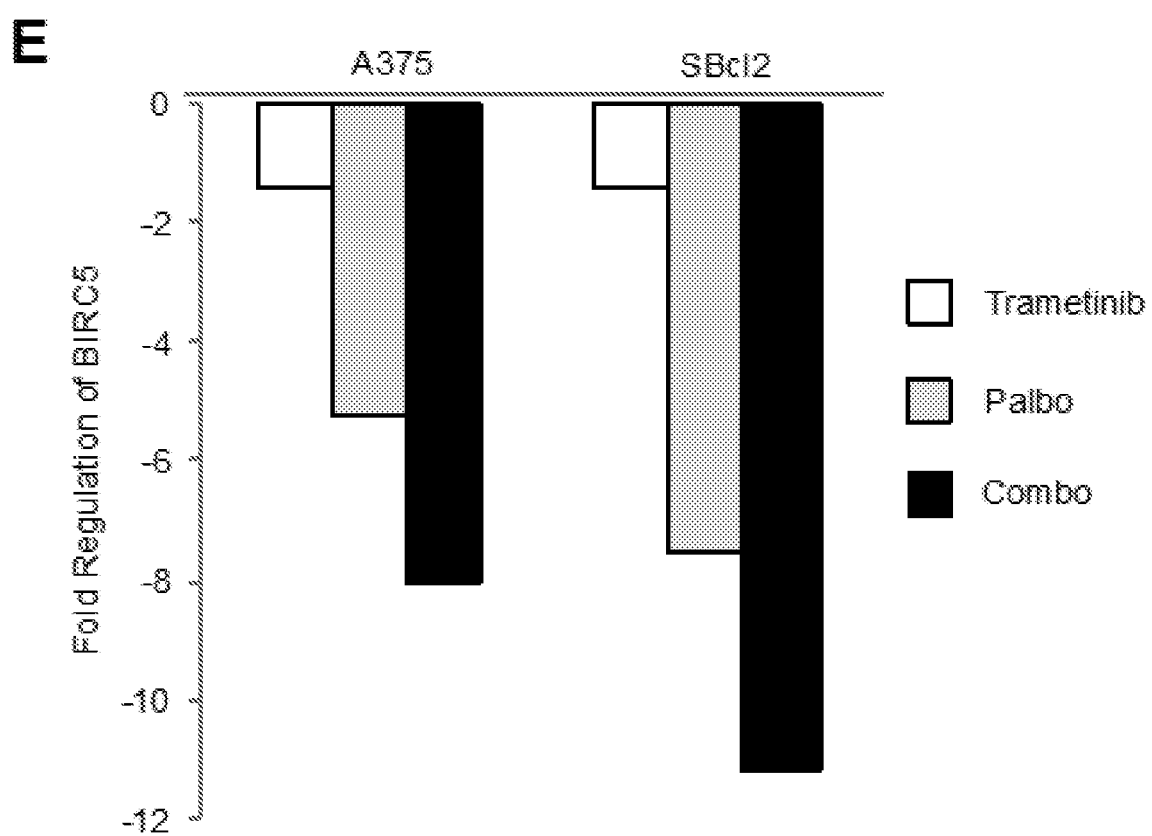
Figure 5F:
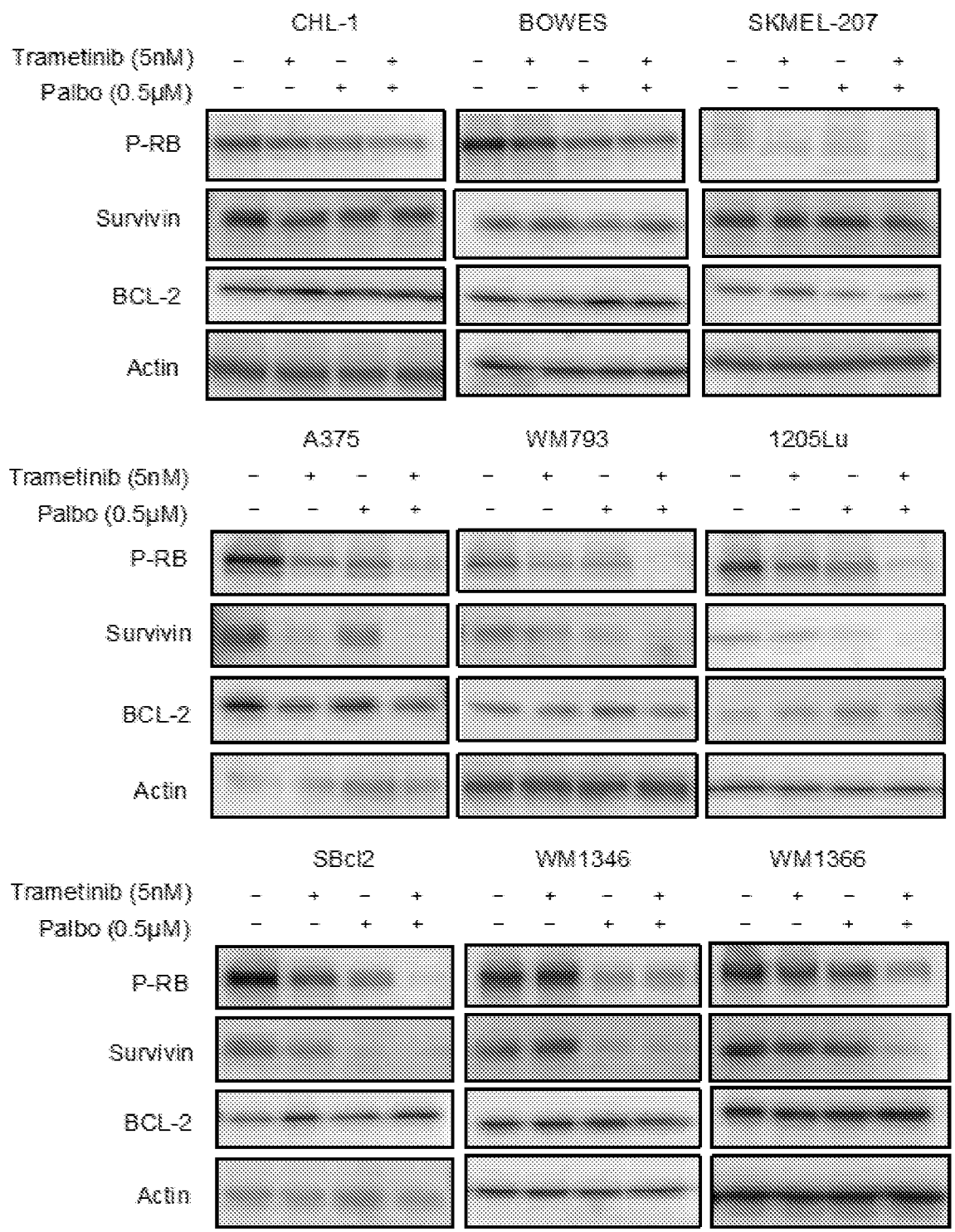

Since Bim-EL was induced by MEK inhibition alone, the mechanistic basis of the drug synergy was explored by testing for modulation of apoptotic genes on a quantitative PCR array. Among the 84 survival-related genes, BIRC5 exhibited the greatest change in levels in response to concurrent inhibition of MEK and CDK4/6 that was consistent between the two most sensitive cell lines, A375 and SBcl2 (FIG. 5E). BIRC5 encodes for survivin, a protein belonging to the inhibitor of apoptosis (IAP) family. A similar trend in the modulation of protein levels of survivin by Western blot was validated. Concurrent treatment with trametinib and palbociclib completely ablated the expression of survivin in sensitive mutant BRAF and mutant NRAS cell lines, which coincided with the dephosphorylation of RB1 (FIG. 5F). By contrast, the combination of trametinib and palbociclib did not affect survivin levels in less sensitive lines, CHL-1, BOWES, and SKMEL207 (FIG. 5F). Although expression of the pro-survival protein, BCL2, was modestly affected on the PCR array, there were no alterations at the protein level (FIG. 5F).

Figure 5G:
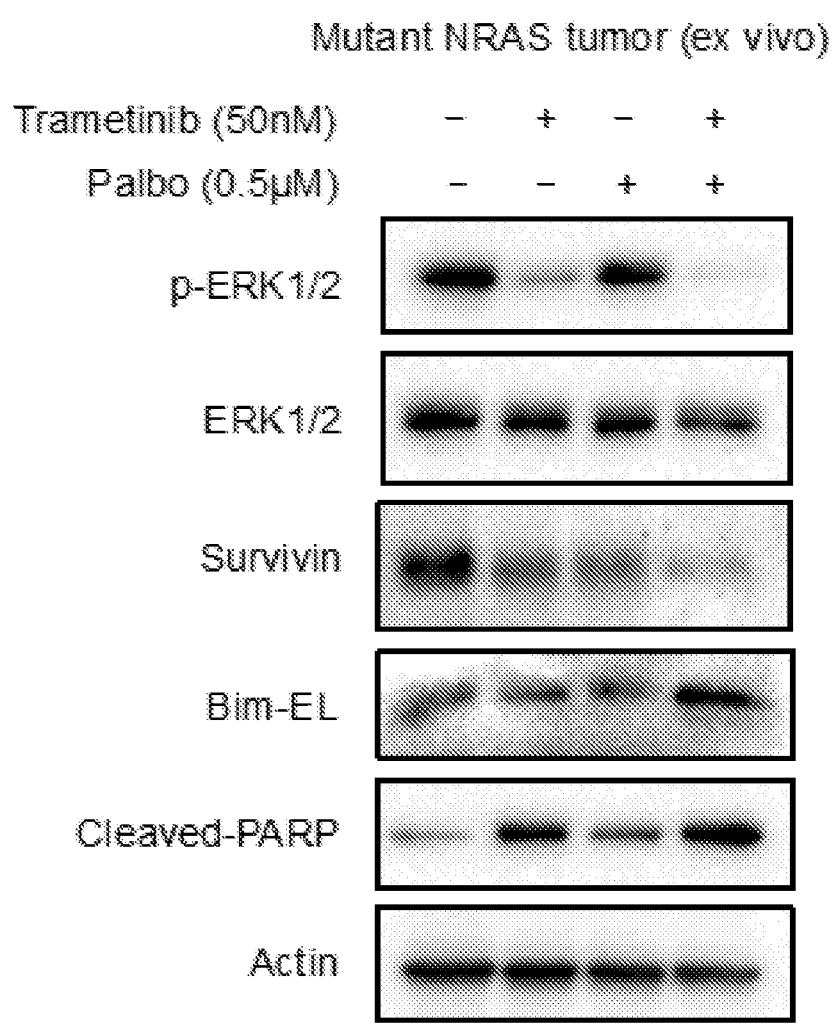

Finally, a primary human tumor explant culture was utilized to interrogate whether the combinatorial treatment led to an enhanced apoptotic response. Ex vivo treatment of NRAS-mutant melanoma tissue for 48 hours with single agents alone led to decreased survivin expression that was further suppressed in combination treated tumors (FIG. 5G). Bim-EL expression and cleaved PARP levels were also enhanced in combination-treated lysates. These data suggest that Bim-EL up-regulation and survivin down-regulation may be markers of the response to CDK4/6 and MEK inhibitor combinations.

Survivin is Essential for the Survival of Melanoma Cells.

Figure 6A:
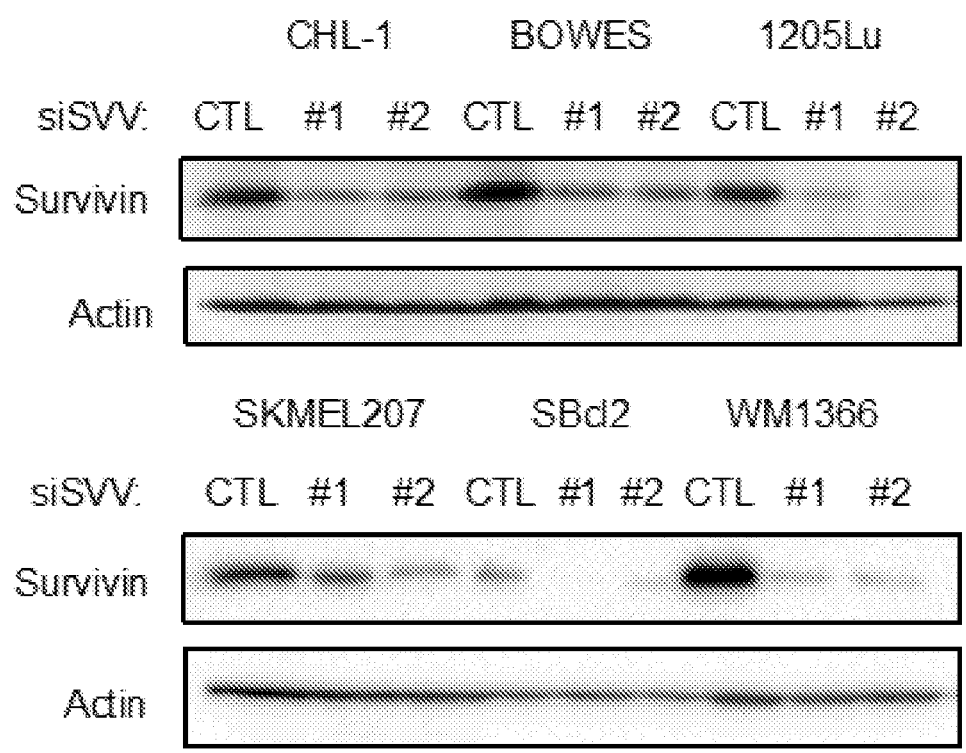
FIGS. 6A-6E depict survivin as essential for the survival of melanoma cells.
Figure 6B:
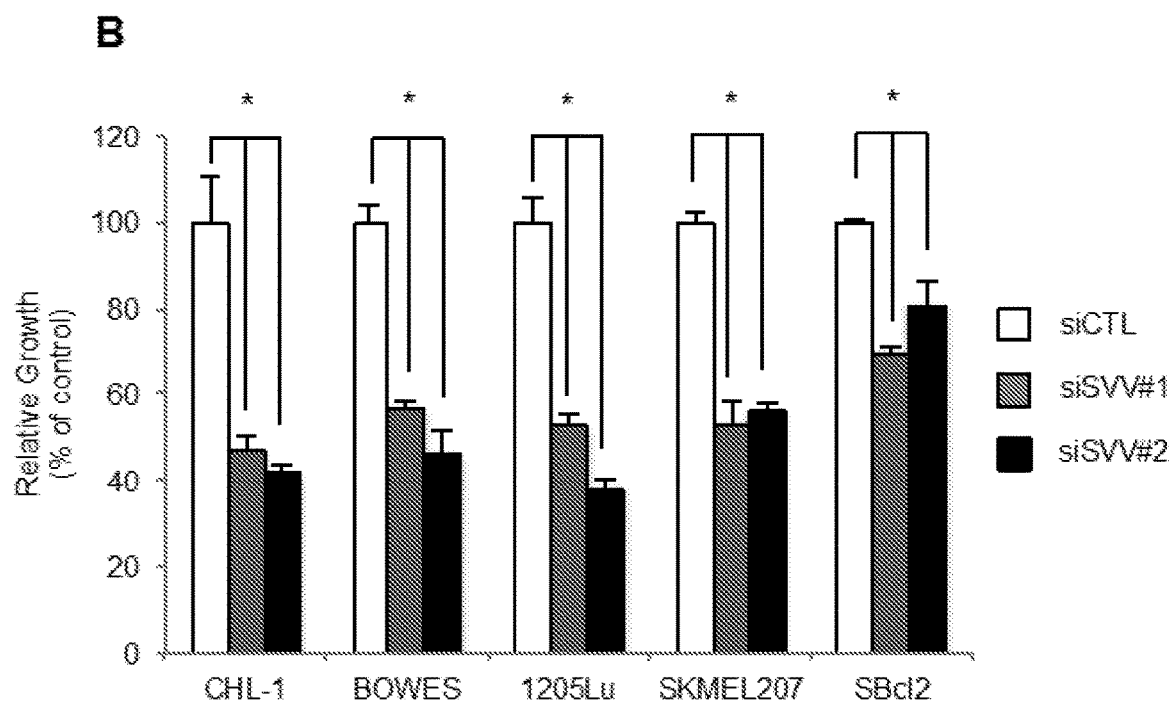
Figure 6C:
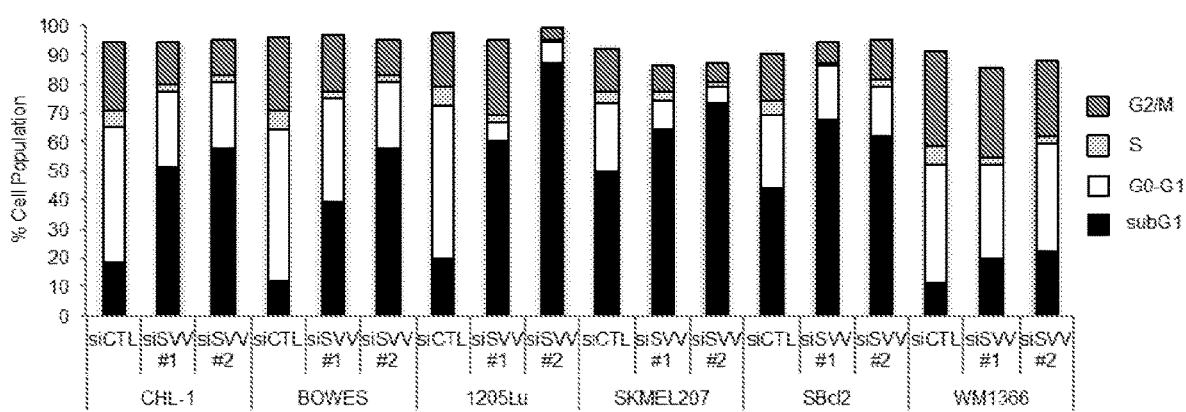
Figure 6D:
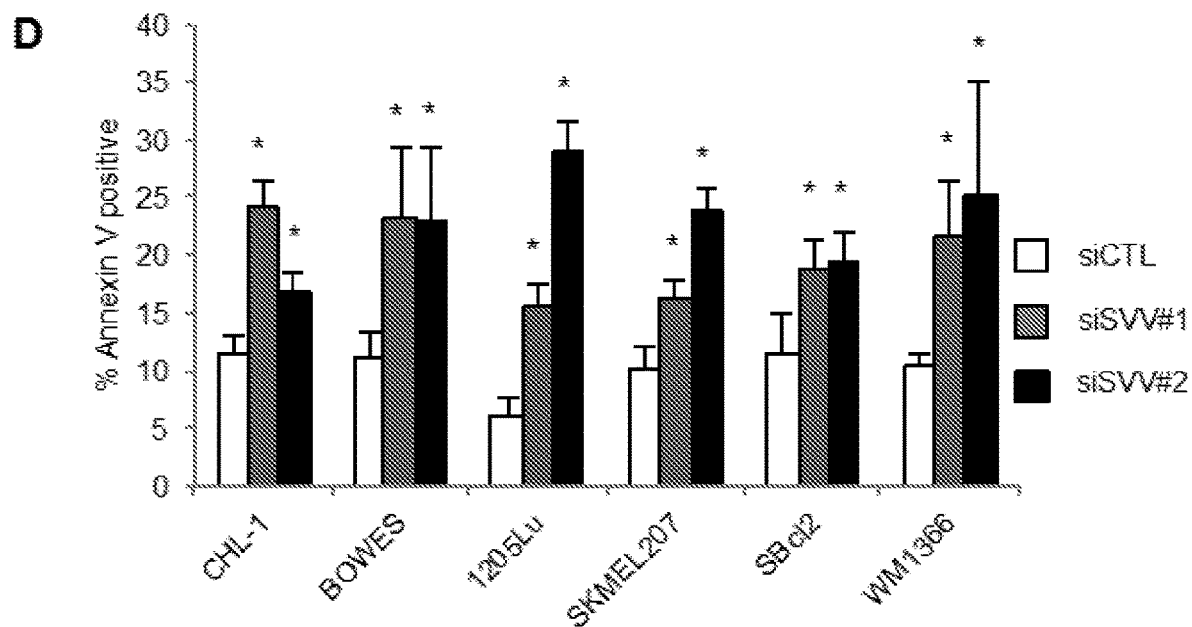
Figure 6E:
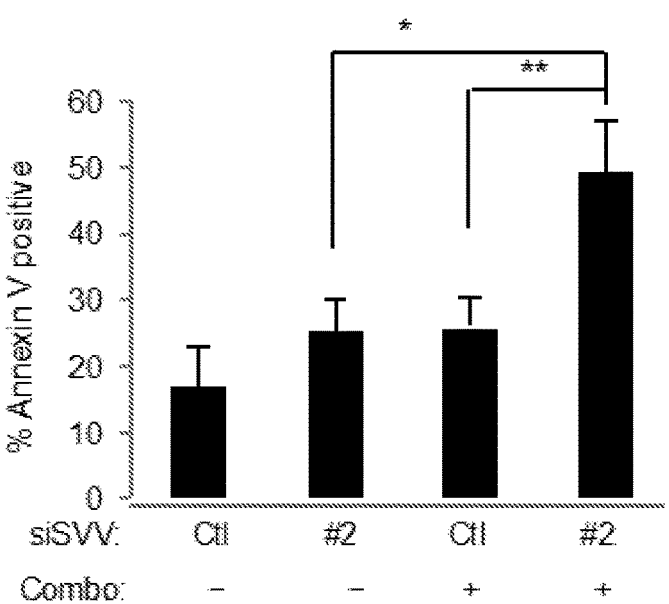

To investigate whether survivin is required for survival, survivin expression was silenced in a panel of melanoma cells (FIG. 6A). Indeed, FIG. 6 depicts that survivin is essential for the survival of melanoma cells. FIG. 6A depicts melanoma cells were transfected with control or survivin-targeting siRNA #1 and #2 for 72 hours and lysates were analyzed by Western blot. FIG. 6B depicts knockdown of survivin leads to decreased cell viability in melanoma cells (n=4, error bars=SD *p<0.01). FIG. 6C depicts cell cycle analysis of melanoma cells after 72 hours of transfection with two distinct siRNA specific for survivin. Bar graphs were generated from averages of three independent knockdown experiments. FIG. 6D depicts that melanoma cells were transfected with control or two distinct survivin-targeting siRNA for 72 hours before they were analyzed for annexin V staining by flow cytometry (n=3, error bars=SD, *p<0.05). FIG. 6E depicts that CHL-1 cells were transfected with control or survivin siRNA before they were treated with either DMSO or the combination of trametinib (5 nM) plus palbociclib (0.5 mM) (n=3, error bars=SD, *p<0.05 **p<0.01).

Knockdown of survivin led to a decrease in cell viability as compared to control transfectants in MTT assays (FIG. 6B). In addition to its role in resistance to apoptosis, mitotic properties of survivin have been described; thus, it was examined whether depletion of survivin leads to cell cycle arrest in G2/M phase or cell death in melanoma cells by PI and annexin V staining. Survivin knockdown in a panel of melanoma cells led to accumulation in the sub-G1 phase post-knockdown indicative of apoptotic cell response but not G2-M accumulation after 72 hours (FIG. 6C). Depletion of survivin at earlier time points (24 hours) did not induce an arrest in G2-M (data not shown). Similarly by annexin V staining, survivin depletion induced significant apoptosis in the majority of the cell lines we tested across different genotypes (FIG. 6D).

Next, it was determined whether knockdown of survivin was capable of sensitizing combination-resistant CHL-1 cells to the CDK4/6-MEK inhibitor combination. Depletion of survivin in conjunction with combination treatment increased cell death in CHL-1 cells (FIG. 6E). These data indicate that survivin depletion regulates the response of melanoma cells to the combination of CDK4/6 and MEK inhibitors.

Combined CDK4/6 and MEK Inhibition In Vivo Potently Inhibits E2F Reporter Activity and Regresses Melanomas.

Figure 7A:
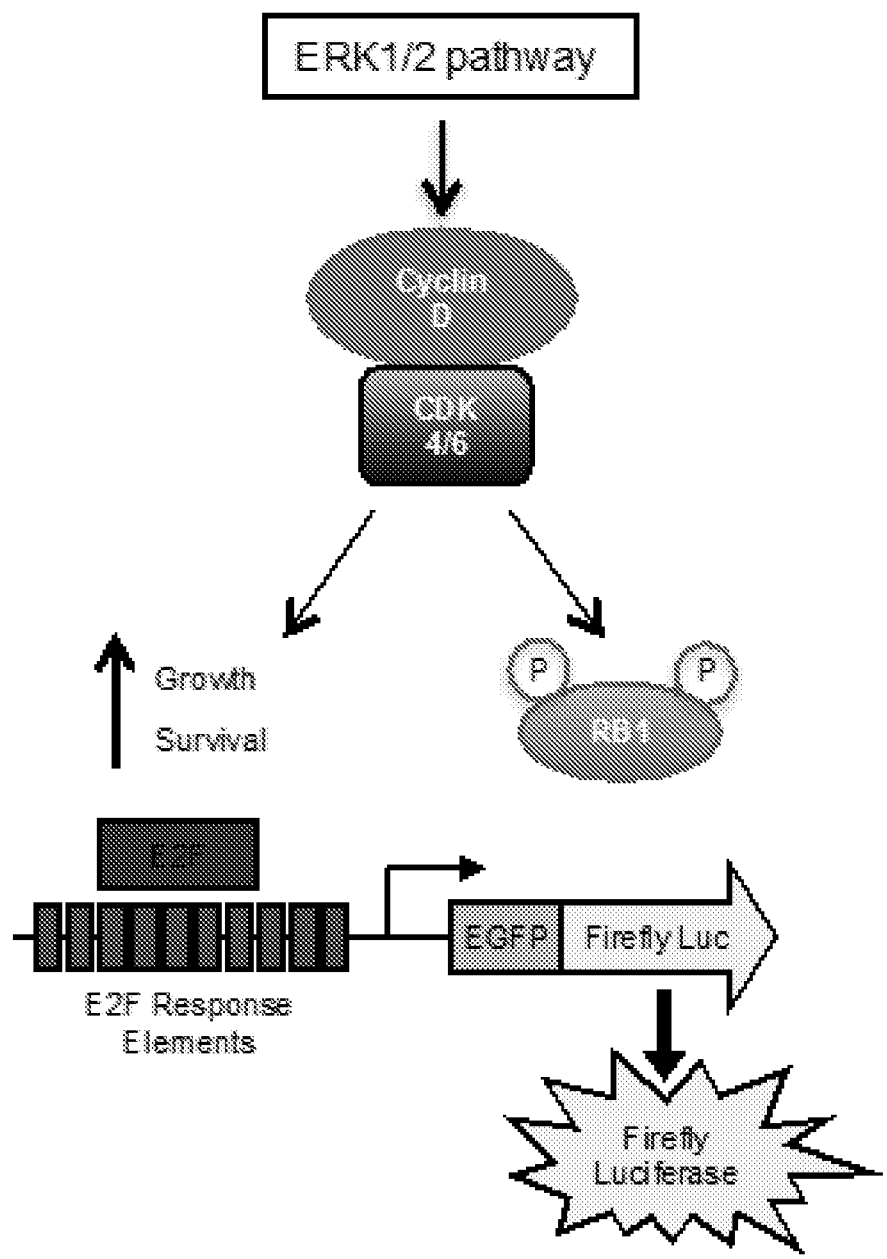
FIGS. 7A-7H depict an embodiment of the E2F reporter model.
Figure 7B:
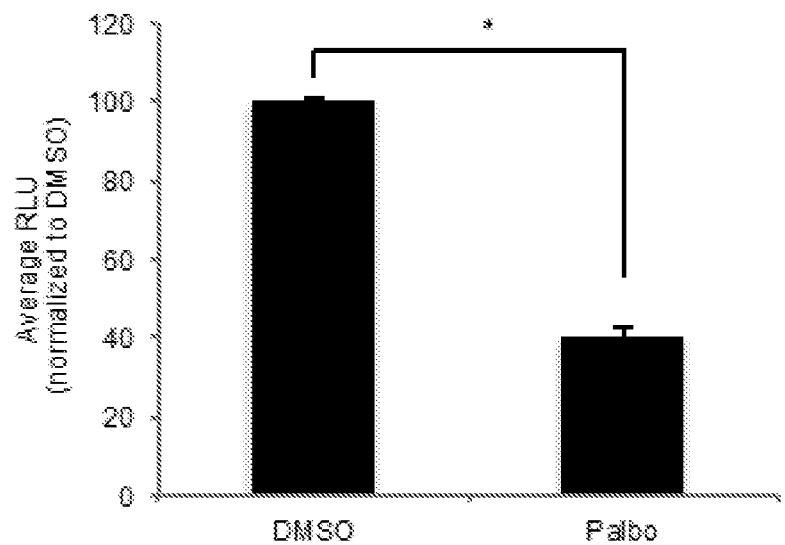
Figure 7C:
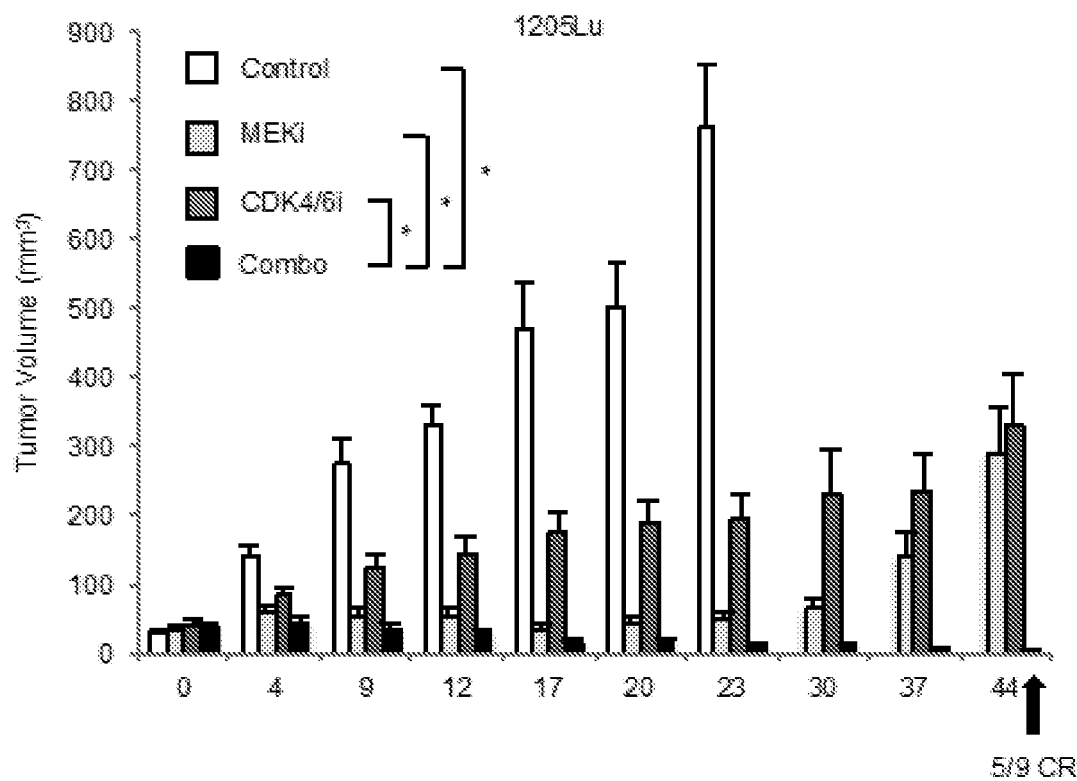
Figure 7D:
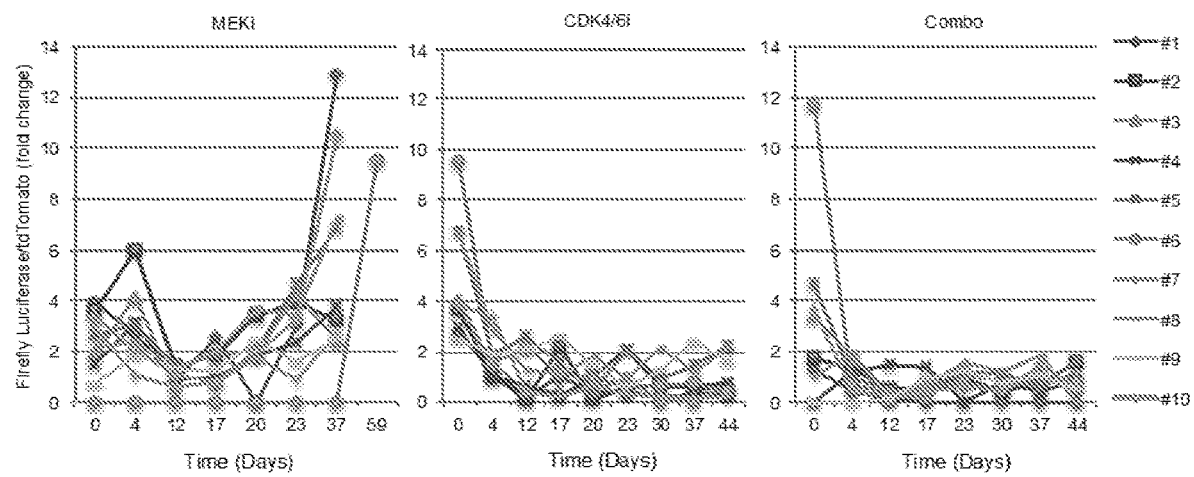
Figure 7E:
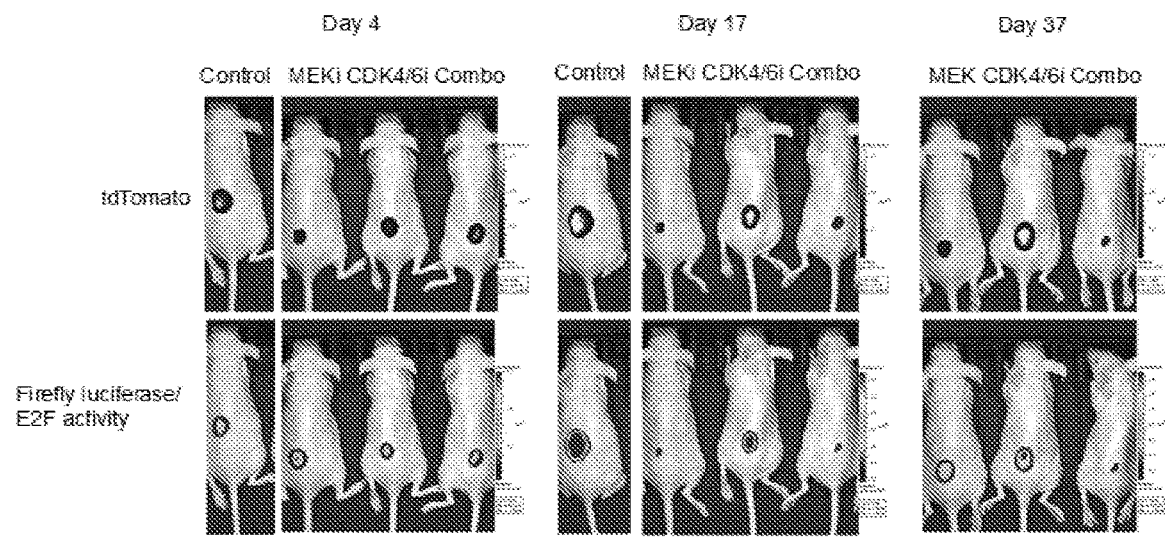
Figure 7F:
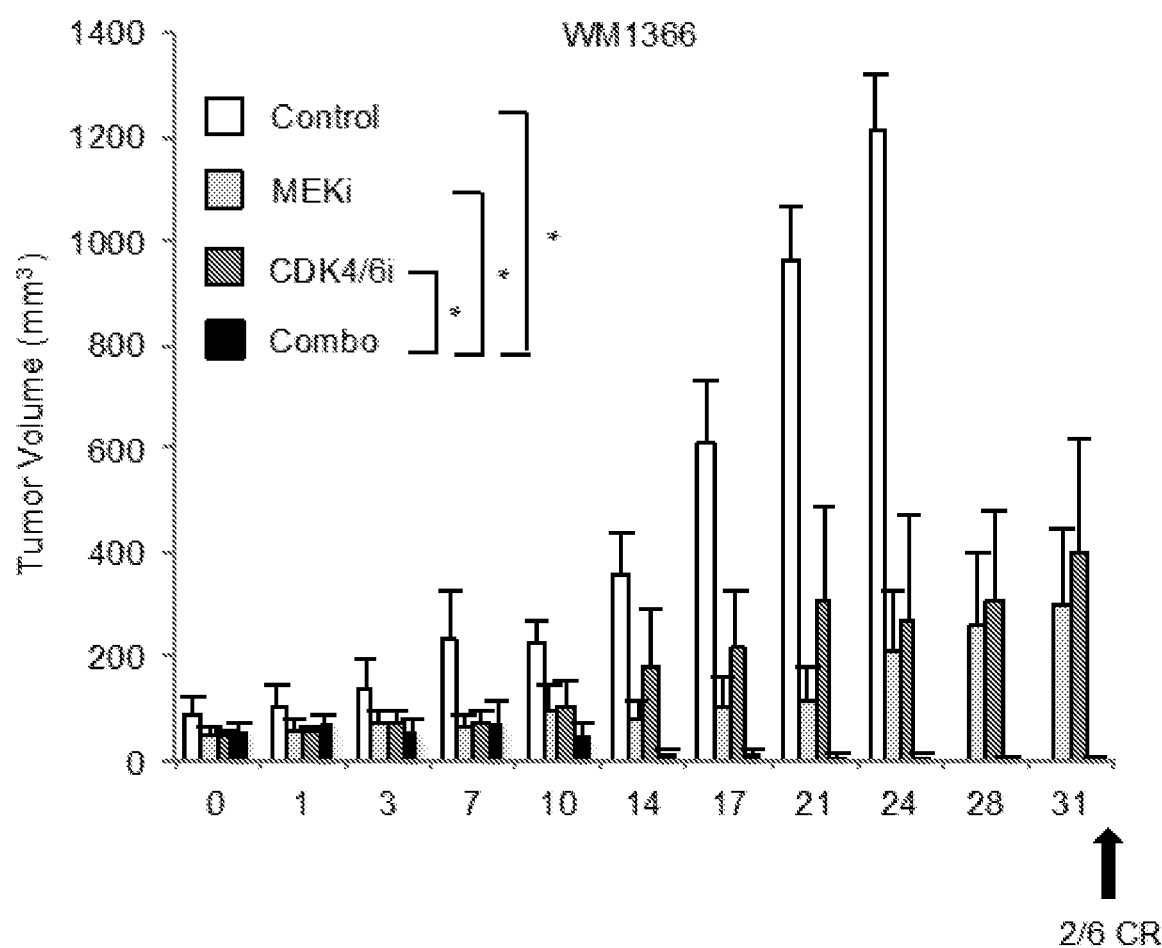
Figure 7G:
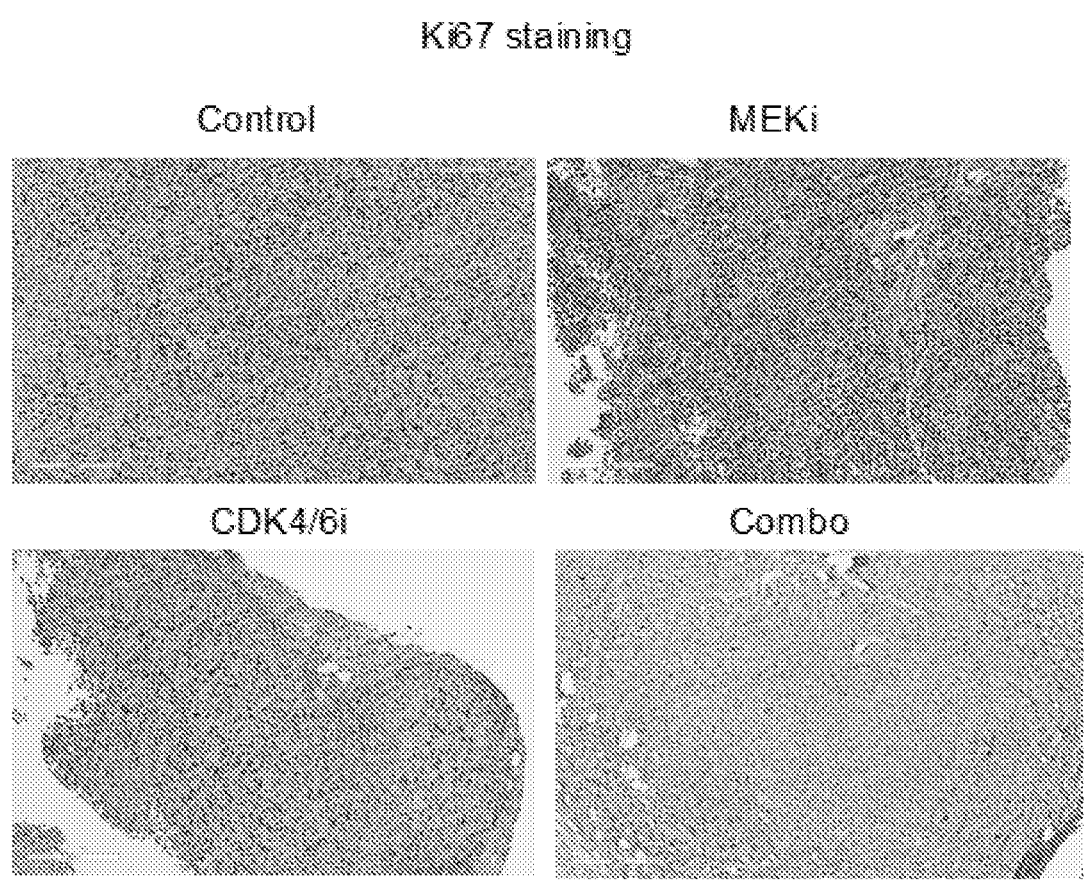
Figure 7H:
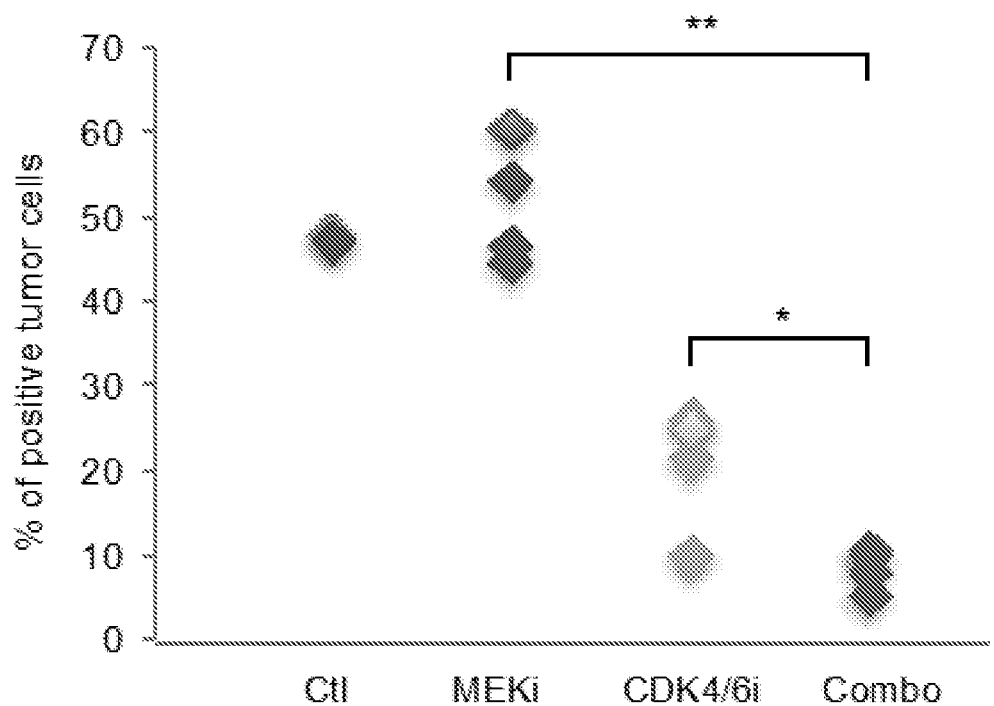

Based on encouraging in vitro data suggesting the benefit of combined CDK4/6 and MEK inhibition, the studies were extended in vivo. FIG. 7 depicts that the combination of CDK4/6 and MEK inhibition is synergistic in vivo. FIG. 7A depicts the E2F reporter system for measuring the efficacy of CDK4/6 and MEK inhibitors in vivo. Firefly luciferase is expressed under the control of E2F response elements. FIG. 7B depicts that 1205LuTR reporter cells were treated with DMSO or palbociclib (0.5 μM) for 48 hours (error bars=SD, *p<0.001, n=3). FIG. 7C depicts that mice bearing 1205Lu xenografts were treated with control, MEK inhibitor (PD032901) alone, CDK4/6 inhibitor (palbociclib) alone, or in combination. Tumor volume was measured by digital caliper (error bars=SEM, *p<0.001 comparing combo to single agents and control). CR=complete response. FIG. 7D depicts analysis of E2F reporter activity normalized to tdTomato fluorescent protein activity in 1205Lu xenografts. FIG. 7E depicts images from individual mice bearing 1205Lu xenografts with tumor progression associated with high E2F reactivation in MEK inhibitor-treated mice and low E2F reactivation in CDK4/6 inhibitor and combo-treated inhibitor mice. FIG. 7F depicts mice bearing WM1366 xenografts were treated with control, MEK inhibitor (PD032901), CDK4/6 inhibitor (palbociclib), or in combination. Tumor volume was measured by digital caliper (error bars=SE, *p<0.001 comparing combo to single agents and control). CR=complete response. FIG. 7G depicts representative images of 1205Lu xenografts taken from mice fed vehicle, MEK inhibitor, CDK4/6 inhibitor and combo-laced chow analyzed for Ki67. FIG. 7H depicts quantitation of Ki67 positive cells (% of total cells) taken from mice fed vehicle (n=2), MEK inhibitor (n=4), CDK4/6 inhibitor (n=4) and combo laced chow (n=4). Combo versus single regiments, *p<0.05, **p<0.001.

To test the inhibition in vivo, the E2F-dependent luciferase reporter cell line was developed to enable temporal quantification of the effects of CDK4/6 inhibitor based treatments in a quantitative, non-invasive, and tumor-selective manner. In this reporter system, hyper-phosphorylation of RB1 leads to the uncoupling of E2F and E2F-mediated induction of firefly luciferase activity (FIG. 7A). 1205Lu cells were chosen based on their ability to form tumors in vivo and their utility in a previously developed ERK1/2 reporter system.

Figure 8:
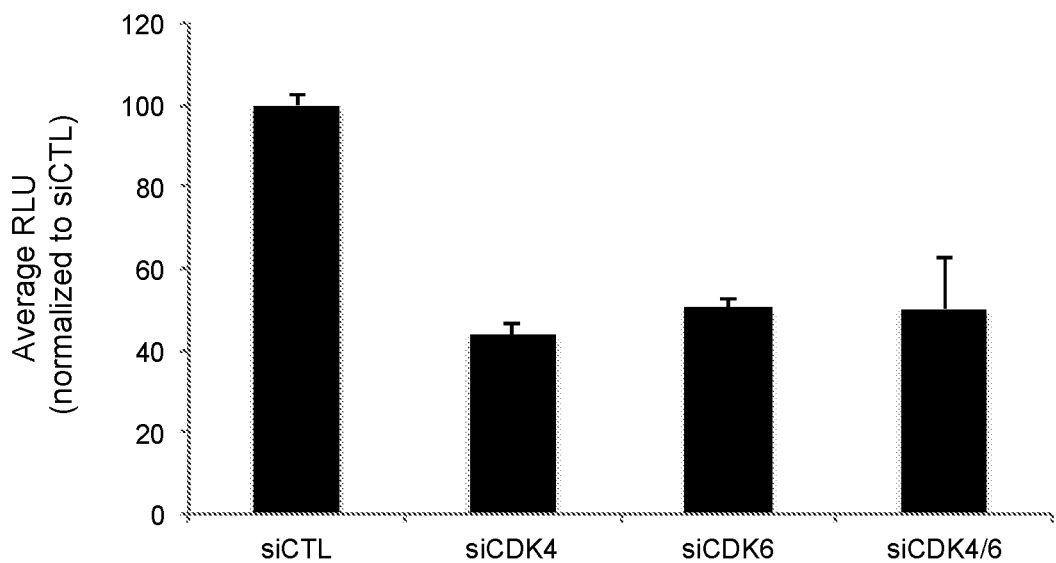
FIG. 8 depict an in vitro screen with silencing RNA to CDK4 and CDK6 utilizing 1205Lu E2F reporter cells.

Tumor cells were also transduced with tdTomato fluorescent protein to selectively monitor tumor growth. In vitro, 1205Lu reporter cells showed a 60% reduction in firefly luciferase activity when normalized to actin levels in the cells following 48 hours of treatment with palbociclib (FIG. 7B). Silencing RNA targeted to CDK4 and/or CDK6 also resulted in >50% decrease in firefly luciferase activity (FIG. 8). In FIG. 8 1205Lu reporter cells were transfected with silencing RNA to control sequence, CDK4, CDK6 or both CDK4 and CDK6. After 72 hours of transfection, whole cell lysates were collected and luciferase activity was measured in each sample. Firefly luciferase activity was normalized to actin levels in each sample.

This system can be used for a high throughput screening of potential inhibitors prior to their utility in vivo. Those of ordinary skill in the art will recognized that the reporter cells as described herein can be utilized in one of many screening protocols using individual slides and cells or in multi-welled plates to increase throughput. Mechanisms to quantify and visualize the cells in these individual plates are well known to those of skill in the art, in addition to the examples and methods described herein.

In a preferred embodiment, a pre-determined number of cells can be transferred to a well and treated with a compound of interest and a carrier vehicle. A further well can be treated with just the drug vehicle to serve as a control, as is known to one of ordinary skill in the art. Suitable replicates can be included, and/or several different compounds of interest can be tested at a time. The treated cells are then incubated as described herein, typically for between 12-72 hours and then luminescence is measured to determine the amount of pathway activity. Suitable luminometers is known to one of ordinary skill in the art, and is able to quantify luciferase activity for each well and therefore calculate the efficacy of the compound as compared to the control.

The benefit to a screening model in vitro is that it can be further verified by use of the same cells in vivo. Indeed, a hypothetical set of 1000 compounds can be quickly and easily screened for efficacy and these compounds can be quantified based on the ability of the compound to block CDK4/6-E2F pathway. As known to one of ordinary skill in the art, superior compounds can be re-tested to confirm efficacy in a further in vitro test, or can be then further tested in in vivo models such as a mouse xenograft model. These models will also test for efficacy of block of E2F pathway, but also to confirm and test for resistance to the drug. Resistance to the compound of interest can be tested by monitoring firefly luciferase activity and tdTomato activity in a temporal manner and looking for an increased in the value of firefly luciferase activity normalized to tdTomato fluorescence which indicates that the E2F pathway has been reactivated and thus, progression of the cell cycle.

Indeed, in a performed xenograft mouse model, 1205Lu reporter cells were intradermally injected into immunodeficient nude mice. Tumors were allowed to form before treatment with control chow, MEK inhibitor (PD0325901) chow, CDK4/6 inhibitor (palbociclib) chow or chow containing both inhibitors. In the single agent and combination treatment cohorts, there was suppression of reporter activity that was more rapid in the CDK4/6 inhibitor-based treatments (FIGS. 7B and 7C). While MEK inhibitor initially maintained tumor volumes at a static level and even led to one complete regression (mouse #6), dramatic tumor regrowth was detected by treatment day 44 that was frequently preceded by strong E2F reactivation (FIGS. 7B and 7C). Tumors from mice treated with CDK4/6 inhibitor alone showed low but continuous growth with persistent inhibition of the E2F pathway (FIGS. 7B and 7C). Levels of E2F activity also remained low in tumors from mice treated with the combination of MEK plus CDK4/6 inhibitor and this regimen was the only treatment to produce significant tumor regressions in 1205Lu xenografts (FIGS. 7B, 7C and 7D). Although combining inhibitors can induce toxicities, the weight of the mice in all four cohorts was comparable from the starting time to the time of termination.

Similar results on tumor growth were observed with a second reporter model in an NRAS-mutant melanoma background (FIG. 7E). In contrast to the 1205Lu model, the response of WM1366 tumors to single agent treatment groups were heterogeneous. However, combination treatment resulted in uniform tumor regressions and resulted in two out of six complete responses (FIG. 7E). E2F activity was diminished in the tumor (mouse #7) that showed complete response to the combination treatment. Fluctuations in E2F activity occurred in one tumor that did not completely regress (mouse #1) and E2F reactivation also preceded the increase in tumor volume/tdTomato activity in combination-resistant tumors (mouse #2 and #5).

Analyses of the harvested tumors from the 1205Lu reporter model revealed a statistically significant decrease in proliferating Ki67 positive cells in combination treated samples when compared to single agent and control treated tumors (FIG. 7F, 7G). Together, these data show that an E2F reporter xenograft model may be used to quantitate drug target inhibition and its association with tumor growth inhibition in vivo. Furthermore, the combination of a MEK inhibitor with palbociclib provides an effective therapeutic strategy for BRAF and NRAS-mutant melanomas.

E2F Reactivation and Rapid Tumor Regrowth from Combo Drug Withdrawal.

Figure 9A:
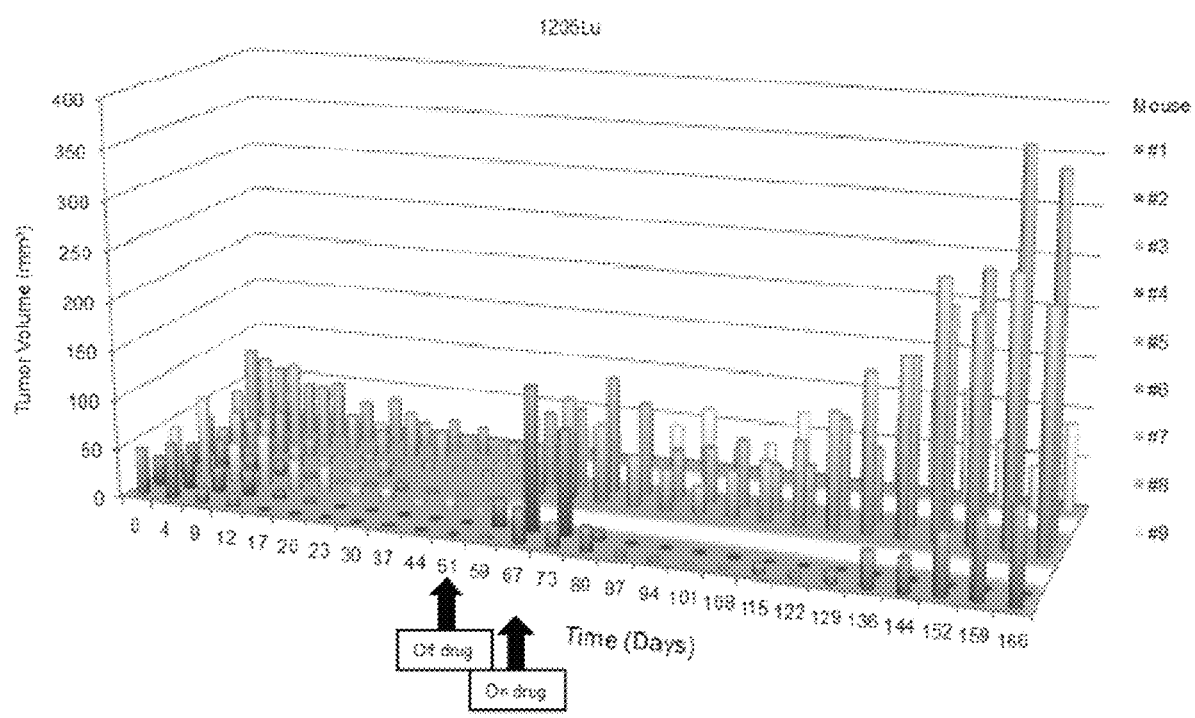
FIGS. 9A-9C depicts tumor regrowth following MEK and CDK4/6 inhibitor withdrawal. E2F reactivation precedes tumor regrowth following withdrawal.
Figure 9B:
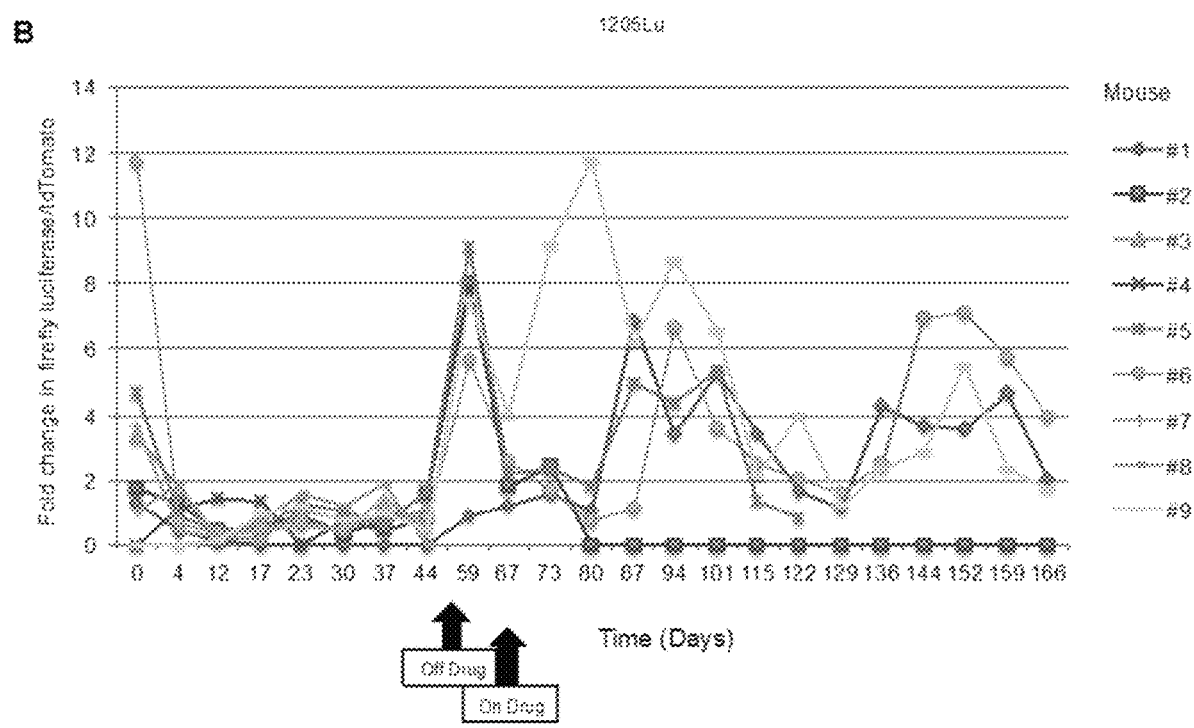
Figure 9C:
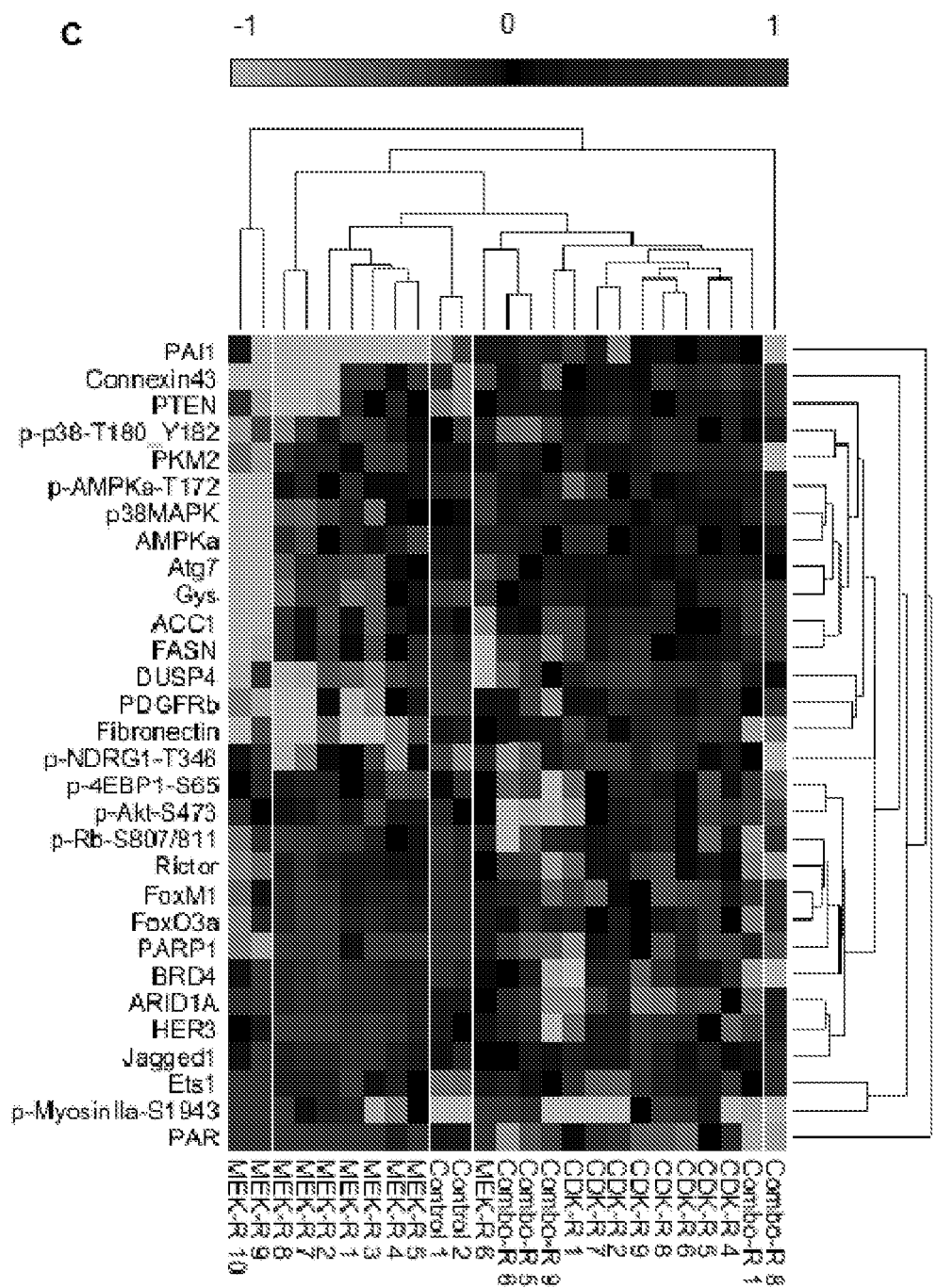

In the 1205Lu reporter model, five out of nine mice treated with the palbociclib/MEK inhibitor combination achieved complete response, as defined by undetectable caliper measurements (FIG. 9A); however, weak tdTomato signal ($<0.8\times10^{10}$ p/sec/cm$^2$/sr) was detected in position of the tumors in all five mice. As depicted in FIG. 9, tumor regrowth following MEK and CDK4/6 inhibitor withdrawal is identified. FIG. 9A depicts mice bearing 1205Lu xenografts that showed complete response from the combination therapy were removed from treatment at day 51 and monitored for durable response. Mice were retreated with combination regimen at day 67. FIG. 9B depicts modulation of E2F activity in combination treated mice following drug removal and retreatment. E2F reactivation is predictive of tumors that would later acquire resistance to the combination treatment. The tumor from mouse #5 exhibited necrosis by day 129 and was excluded from luciferase and tdTomato analysis. FIG. 9C depicts RPPA analysis on resistant tumors. Combination resistant tumors clustered with CDK inhibitor resistant tumors using unsupervised hierarchical clustering. ComboR 8 is a regressing tumor that was isolated during regression on treatment. MEKR 9/10 was least similar to any other groups. Thus, the E2F reporter melanoma cell line that can be used to screen multiple compounds of interest.

To determine whether the complete responses were durable, these five mice were released from drug treatment (treatment day 51). Within one week off drug, a rapid reactivation of the E2F pathway and tumor regrowth were observed in all mice except one (mouse #1) (FIG. 9B). After two weeks (treatment day 67), mice were retreated with the palbociclib/MEK inhibitor combination. The tumors re-responded rapidly to the combination drug as evident by dramatic inhibition of pathway activity. Overall there was only one complete response with no palpable tumor, residual tdTomato signal or E2F activity (mouse #2). Fluctuations in E2F activity was observed in the other four remaining mice followed by tumor regrowth. Reactivation of the pathway was evident and predictive of tumors that would later acquire resistance to the combination therapy (e.g. mouse #6). These data suggest that residual disease remains after first-line treatment with the CDK4/6 and MEK inhibitor combination and that tumors that regrow from residual disease off drug are likely to acquire resistance following retreatment.

Finally, RPPA data was utilized to identify proteins regulated by tumor resistance. However, it was unclear whether the combination resistant group could be stratified to any single agent resistant group. To determine resistance, all the samples were clustered based on a list of significant antibodies to reduce noise from random differences between groups. This separated the tumors into two major distinct clusters (FIG. 9C). Notably, combination resistant tumors that regrew from subsequent withdrawal and retreatment of the inhibitors formed a clear cluster with CDK inhibitor resistant tumors. MEKR #9/#10 and Combo-R #8 formed their own clusters, as well as the control samples. Combo-R #8 was a sample that regressed on-treatment and was isolated during regression. Taken together, these data suggest that combination resistant tumors were molecularly similar to tumors that slowly progressed on palbociclib.

By taking melanoma cells modified to express an E2F reporter, the applicants were able to test inhibitory compounds for effect on the tumor and therefore certain methods using the modified cells as described herein, may be suitable for testing of inhibitory compounds. The applicants utilized several compounds, including palbociclib (PD0332991) a selective inhibitor of CDK4/6 that inhibits G1-S progression in vitro thus eliciting a cytostatic effect on tumors. Indeed, there reporter cell lines enable testing of the combined effect of multiple compounds on a reporter cell, or to test several individual compounds under high-throughput screening methods.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

What is claimed is:

1. A kit for testing and determining the efficacy of a compound of interest to inhibit E2 Factor (E2F) activity comprising:
   a reporter cell line, wherein the reporter cell line comprises a 1205Lu melanoma cancer cell line transduced with
   (1) a first lentiviral vector encoding an EGFP-Firefly luciferase fusion gene under the control of E2F transcriptional response elements, and
   (2) a second lentiviral vector encoding tdTomato fluorescent protein.

2. A method of testing the efficacy of a compound of interest to inhibit E2F activity comprising applying the compound of interest to a reporter cell line, wherein the reporter cell line comprises a 1205Lu melanoma cancer cell line transduced with
   (1) a first lentiviral vector encoding an EGFP-Firefly luciferase fusion gene under the control of E2F transcriptional response elements, and
   (2) a second lentiviral vector encoding tdTomato fluorescent protein.

3. A method of testing the efficacy of a compound of interest to inhibit E2F activity comprising applying at least two compounds of interest to a reporter cell line, wherein the reporter cell line comprises a 1205Lu melanoma cancer cell line transduced with
- (1) a first lentiviral vector encoding an EGFP-Firefly luciferase fusion gene under the control of E2F transcriptional response elements, and
- (2) a second lentiviral vector encoding tdTomato fluorescent protein.

4. The method of claim 2, further comprising incubating the reporter cell line after applying of the compound of interest.

5. The method of claim 4, wherein the amount of firefly luciferase activity is compared to the amount of tdTomato activity in the reporter cell line.

6. The kit of claim 1, wherein the reporter cell line is suitable for use in vitro or in vivo.

* * * * *